(12) United States Patent
Tovar et al.

(10) Patent No.: US 8,853,349 B2
(45) Date of Patent: Oct. 7, 2014

(54) DISORDERED ORGANIC ELECTRONIC MATERIALS BASED ON NON-BENZENOID 1,6-METHANO[10]ANNULENE RINGS

(71) Applicant: The Johns Hopkins University, Baltimore, MD (US)

(72) Inventors: John D. Tovar, Baltimore, MD (US); Benjamin C. Streifel, Puyallup, WA (US); Patricia A. Peart, Midland, MI (US)

(*) Notice: Subject to any disclaimer, the term of this patent is extended or adjusted under 35 U.S.C. 154(b) by 0 days.

(21) Appl. No.: 13/715,310

(22) Filed: Dec. 14, 2012

(65) Prior Publication Data
US 2014/0166987 A1 Jun. 19, 2014

(51) Int. Cl.
*C08G 75/00* (2006.01)
*H01L 51/00* (2006.01)

(52) U.S. Cl.
CPC ........ *H01L 51/0071* (2013.01); *H01L 51/0068* (2013.01); *H01L 51/0036* (2013.01)

USPC ............. 528/377; 528/407; 528/163; 528/94; 528/117; 528/118; 528/360; 528/367; 257/40; 257/E51.012; 257/E51.005; 257/E51.024; 427/331

(58) Field of Classification Search
CPC ........................................................ C08G 73/08
USPC ........... 528/407, 163, 94, 117, 118, 360, 367; 257/40, E51.005, E51.024
See application file for complete search history.

(56) References Cited

PUBLICATIONS

Hardigree et al., Macromolecules 2012, 45, 7339-7349.*

\* cited by examiner

*Primary Examiner* — Shane Fang
(74) *Attorney, Agent, or Firm* — Ward and Smith, P.A.

(57) ABSTRACT

Conjugated polymers and small molecules including the non-planar aromatic 1,6-methano[10]annulene ring structure along with aromatic subunits, such as diketopyrrolopyrrole, and 2,1,3-benzothiadiazole, substituted with alkyl chains in a "Tail In," "Tail Out," or "No Tail" regiochemistry are disclosed.

20 Claims, 9 Drawing Sheets

DISORDERED ORGANIC ELECTRONIC MATERIALS BASED ON NON-BENZENOID 1,6-METHANO[10]ANNULENE RINGS

FEDERALLY SPONSORED RESEARCH OR DEVELOPMENT

This invention was made in part with United States Government support under (DMR-0644727 and DMR-1207259 awarded by the National Science Foundation and DE-FG02-07ER46465 awarded by the Department of Energy (DOE). The U.S. Government has certain rights in the invention.

BACKGROUND

Organic semiconductors have proven to be commercially viable alternatives to traditional inorganic electronic materials for light emitting, charge transporting, and energy harvesting applications that require large area, lightweight, and flexible active materials. High performance polymers suitable for these applications are often designed to foster extensive π-stacking in the solid state, but this characteristic can make the material prone to aggregation, crystallization, and undesired degrees of phase segregation after device fabrication. Zhokhavets, U., et al., Thin Solid Films 2006, 496, 679. In contrast, disordered or otherwise amorphous materials that exhibit thermal stability, Sivula, K., et al., J. Am. Chem. Soc. 2006, 128, 13988; processability, Brabec, C. J. Sol. Energy Mater. Sol. Cells 2004, 83, 273; Yip, H.-L.; Jen, A. K.-Y., Energy Environ. Sci. 2012, 5, 5994; and carrier mobility, Chen, T.-A.; Rieke, R. D., Synth. Met. 1993, 60, 175; Chen, T.-A., et al., J. Am. Chem. Soc. 1995, 117, 233, could be useful for such applications.

More particularly, amorphous materials are desirable for such applications as light emitting diodes and thermoelectrics. Steric interactions within or between conjugated polymers directly influence overall intrapolymer planarity and subsequent interpolymer ordering of the resulting thin-film materials. McCullough, R. D., et al., J. Am. Chem. Soc. 1993, 115, 4910; McCullough, R. D.; Lowe, R. D., J. Chem. Soc., Chem. Commun 1992, 70; McCullough, R. D., et al., Synth. Met. 1995, 69, 279; McCullough, R. D., et al., J. Org. Chem. 1993, 58, 904-912. It is not completely understood, however, how to control by design the effects of such interactions, particularly when attempting to control interpolymer stacking and crystallization. Woo, C. H., et al., J. Am. Chem. Soc. 2008, 130, 16324. Because solution processable polymers generally require some sort of solubilizing groups (often long alkyl chains pendant to the main conjugated chain), steric interactions arising from torsional strain between repeat units that contain them play an important role in disturbing the effective conjugation length of these polymers.

Several structure-property relationships have revealed the effects of solubilizing chain regiochemistry on different polymeric materials. Jayakannan, M., et al., J. Polym Sci., Part A: Polym. Chem. 2002, 40, 251; Mondal, R., et al., J. Mater. Chem. 2011, 21, 1537; Ding, J., et al., J. Polym Sci., Part A: Polym. Chem. 2011, 49, 3374; Lee, S. K., et al., J. Polym. Sci., Part A: Polym. Chem. 2011, 49, 1821. In particular, UV-vis and fluorescence spectroscopy revealed that altering only the position of pendant alkyl chains relative to various aromatic polymer backbone subunits was enough to influence planarity within the conjugated polymer backbone. The effect of poly(3-hexylthiophene) (P3HT) regioregularity on electronic properties is a particularly well studied example. Elsenbaumer, R. L., et al., in Electronic Properties of Conjugated Polymers; Kuzmany, H., Mehring, M., Roth, S., Eds.; Springer Series in Solid State Sciences; Springer: Berlin, 1987; Vol. 76, p 400; Souto-Maior, R. M., et al., Macromolecules 1990, 23, 1268; Zagorska, M., et al., Synth. Met. 1991, 45, 385; Zagorska, M.; Krishe, B. Polymer 1990, 31, 1379; Krishe, B., et al., J. Chem. Soc., Chem. Commun 1987, 19, 1476. See also, McCullough, R. D., Adv. Mater. 1998, 10, 93, for a review of poly(3-alkylthiophene) regioregularity.

When positioned in a regiorandom fashion, these alkyl chains cause the conjugated aromatic molecules to experience torsional strain and rotate out of coplanarity, thus breaking the conjugation along the polymer backbone. Hong, S. Y., et al., Macromolecules 2001, 34, 6475. Torsional strain was exacerbated when large, sterically demanding electron-accepting units, such as benzothiadiazole and diketopyrrolopyrrole, were incorporated into thiophene-based donor-acceptor polymers. Despite unfavorable torsional interactions, donor-acceptor polymers made up of components bearing relatively large molecular footprints nevertheless exhibit low optical bandgaps and increased charge transfer and/or separation than all-donor or all-acceptor homopolymers. Havinga, E. E., et al., Polym. Bull. 1992, 29, 119; Havinga, E. E., et al., Synth. Met. 1993, 55-57, 299. These studies compared the torsional interactions among planar aromatic molecules and found that, in general, when the alkyl chains were directed away from the most sterically demanding group, the polymers showed a bathochromic shift in absorption and emission spectra to lower energy due to enhanced electronic delocalization.

SUMMARY

The presently disclosed subject matter provides conjugated polymers and small molecules including the nonplanar aromatic 1,6-methano[10]annulene ring structure along with aromatic subunits, such as diketopyrrolopyrrole, and 2,1,3-benzothiadiazole, substituted with alkyl chains in a "Tail In," "Tail Out," or "No Tail" regiochemistry.

In some aspects, the presently disclosed subject matter provides a compound of Formula (I) or Formula (II):

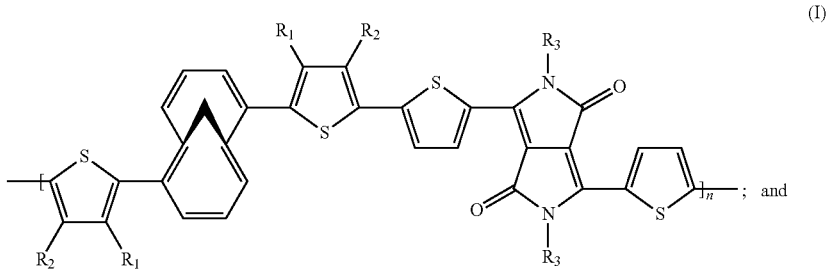

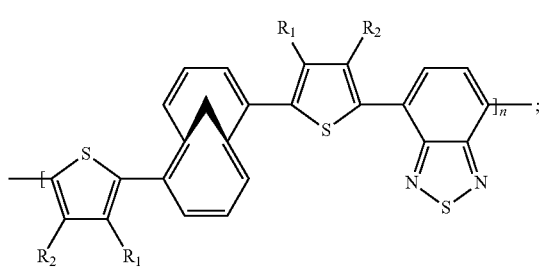

(II)

wherein: n is an integer selected from the group consisting of 1 to 150; and $R_1$, $R_2$, and $R_3$ are each independently selected from the group consisting of H and $C_6$-$C_{20}$ linear or branched alkyl.

When $R_1$ is an alkyl chain, the compounds of Formula (I) and Formula (II) are said to be in a "Tail In" configuration. When $R_2$ is an alkyl chain, the compounds of Formula (I) and Formula (II) are said to be in a "Tail Out" configuration. When both R1 and R2 are hydrogen, the compounds of Formula (I) and Formula (II) are said to be in a "No Tail" configuration.

In certain aspects, the presently disclosed subject matter also provides monomers and oligomers of the compounds of Formula (I) and Formula (II).

In other aspects, the presently disclosed subject matter provides a film comprising a compound of Formula (I) or Formula (II). In certain aspects, the film comprises a blend of a compound of Formula (I) or Formula (II) and one or more of an electron donating material and an electron accepting material. In aspects, the electron accepting polymer comprises a fullerene. In more particular aspects, the fullerene comprises [6,6]-phenyl-$C_{61}$-butyric acid methyl ester (PCBM). In yet more particular aspects, the presently disclosed subject matter provides a device comprising the film of compounds of Formula (I) or Formula (II). In representative aspects, device comprises a bulk heterojunction organic photovoltaic (BHJ-OPV) device.

In other aspects, the presently disclosed subject matter provides a device comprising a compound or film of Formula (I) or Formula (II). Accordingly, in some aspects, the device can be an organic semiconductor, which in some aspects, can comprise a field-effect transistor. Such devices can be used in light emitting, charge transporting, or energy harvesting applications, or as a thermoelectric device, or as components of display elements, electronic tags, electromagnetic sensors, pressure sensors, and the like.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
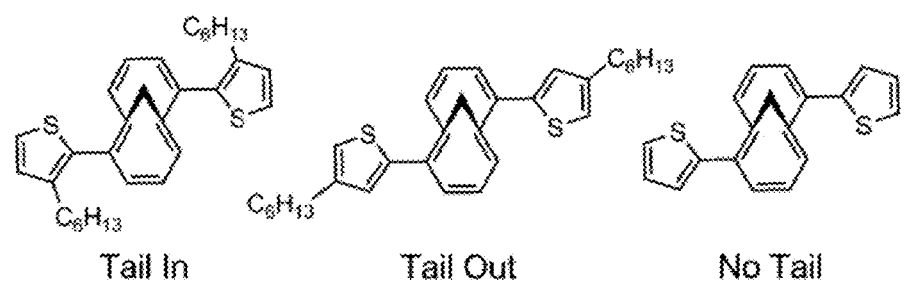
Figure 2:
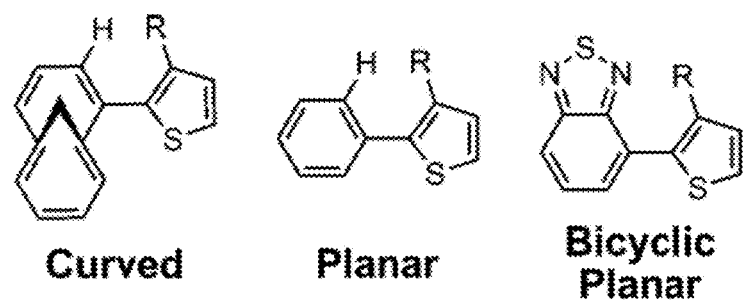
Figure 3:
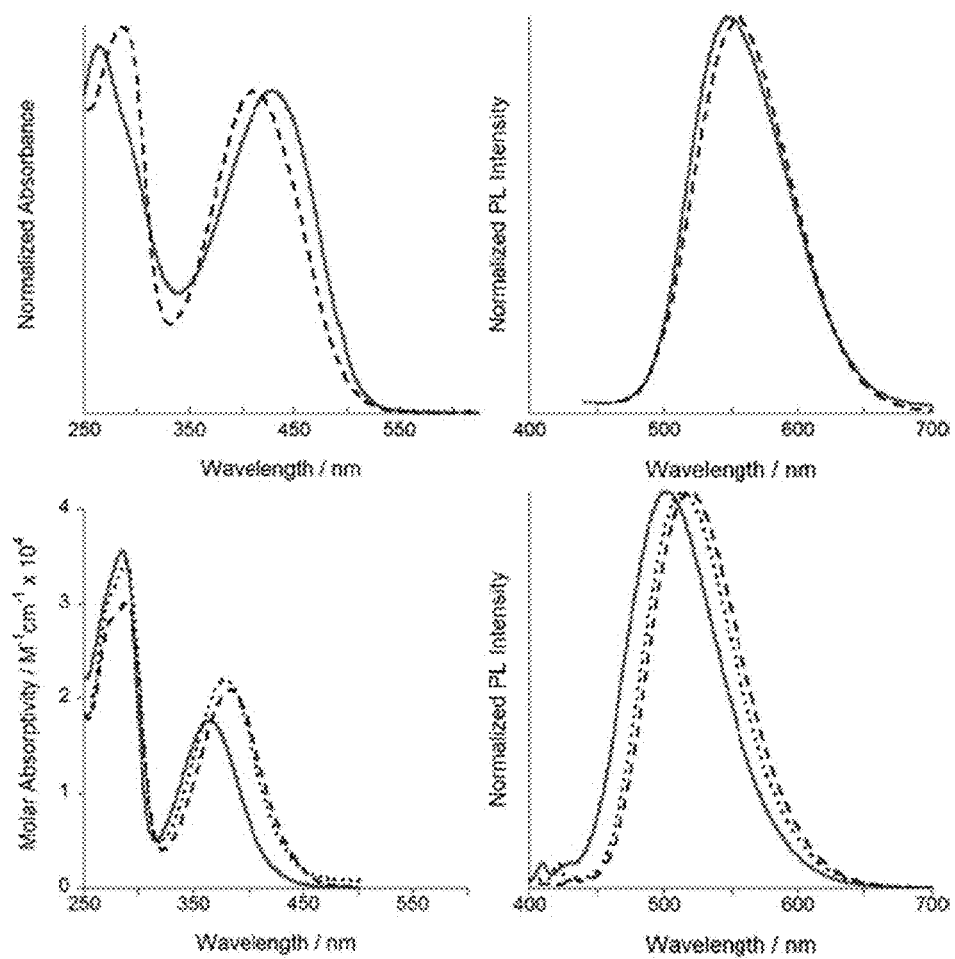
Figure 4:
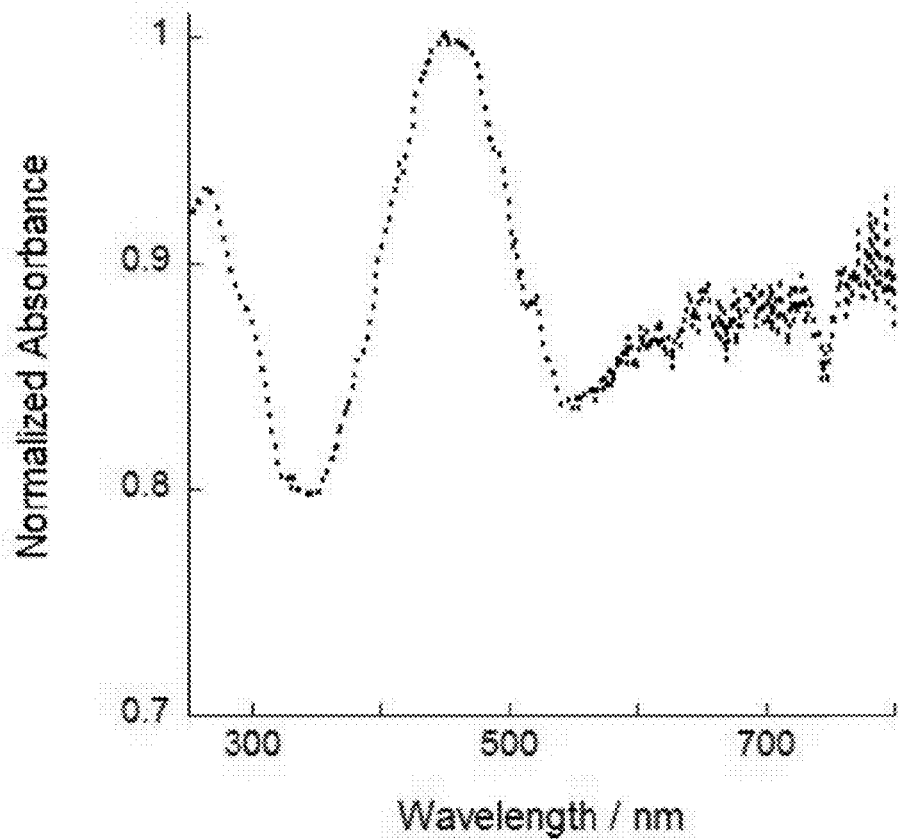
Figure 5:
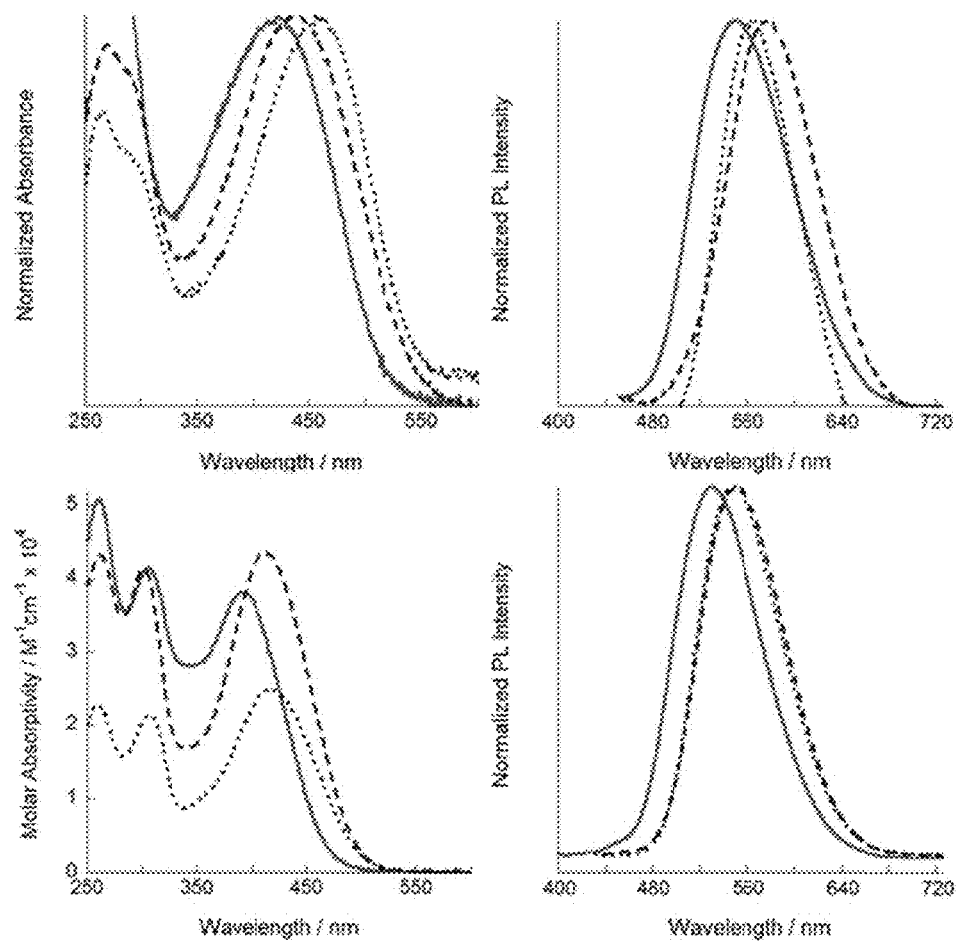
Figure 6:
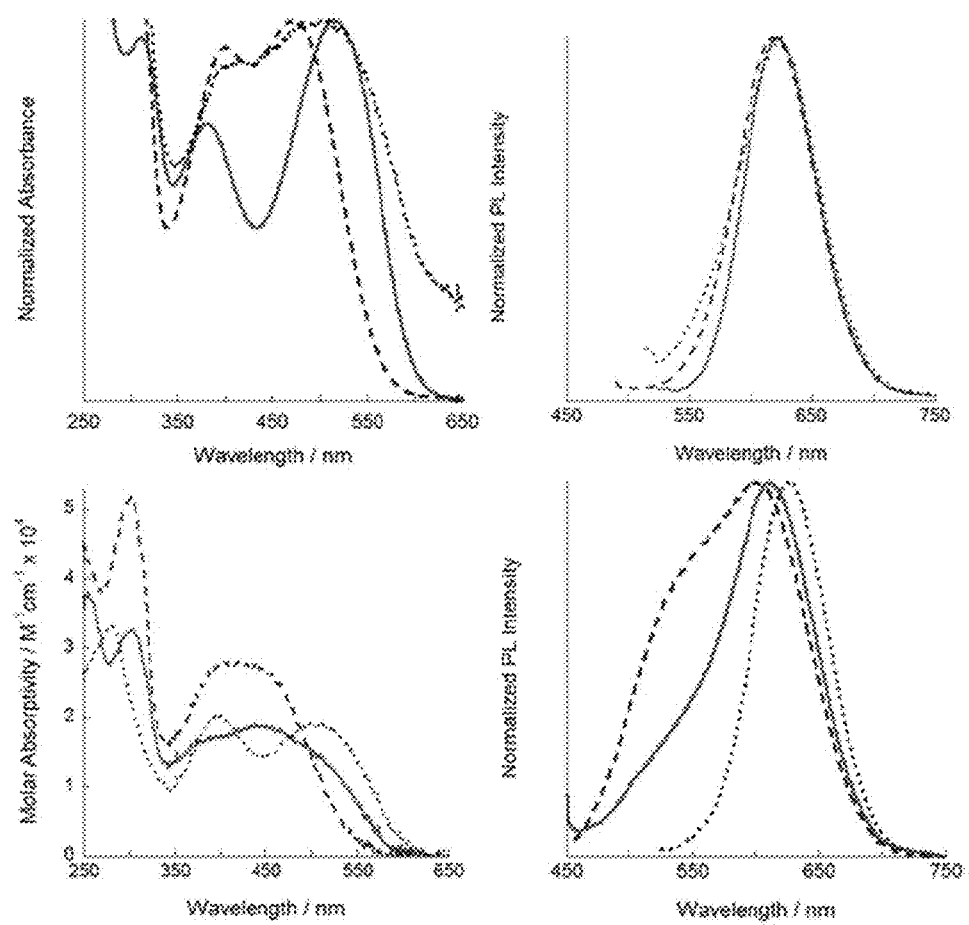
Figure 7:
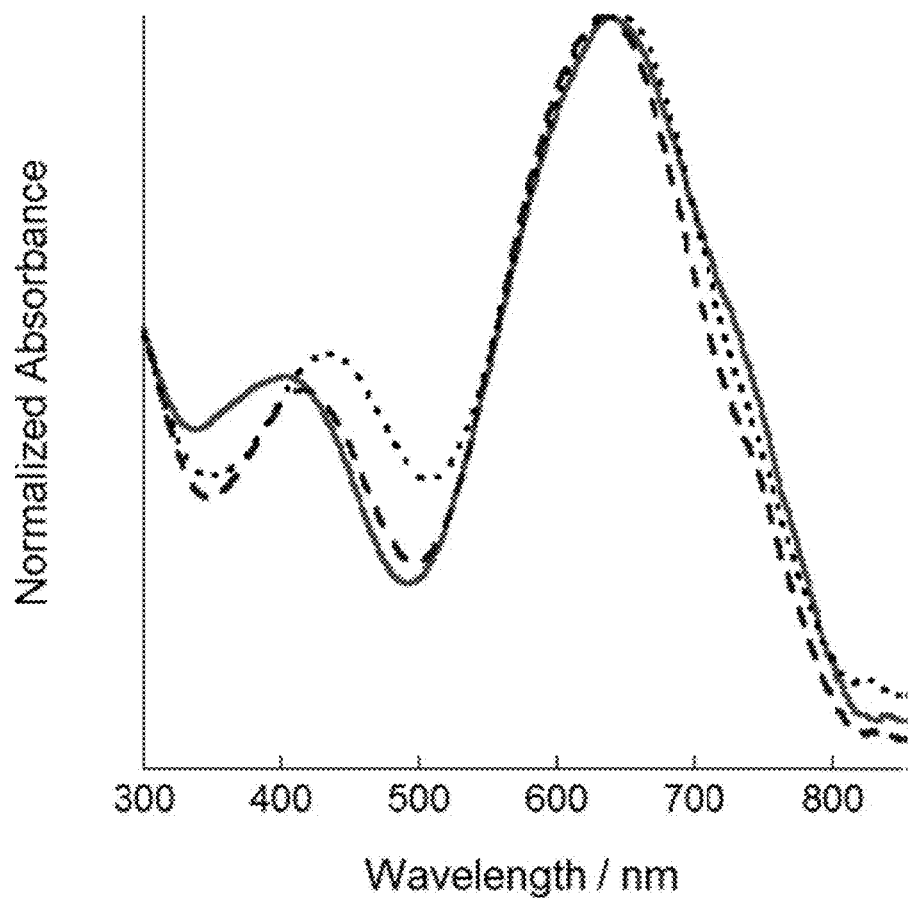
Figure 8:
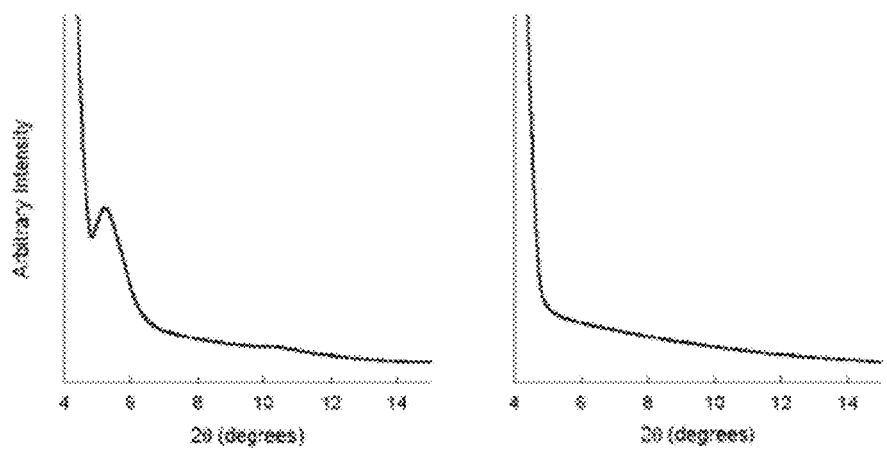
Figure 9:
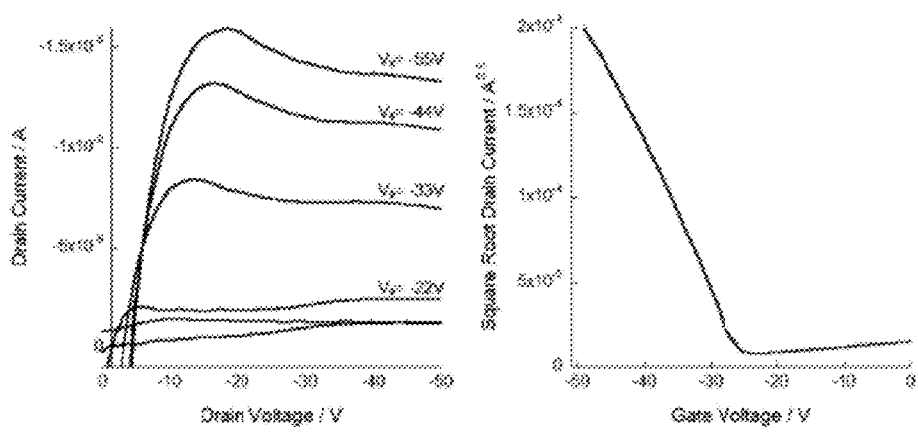

Having thus described the presently disclosed subject matter in general terms, reference will now be made to the accompanying Figures, which are not necessarily drawn to scale, and wherein:

FIG. 1 shows Tail In, Tail Out, and No Tail configurations of representative thiophene-M10A-thiophene (TMT) monomers. The terms Tail In, Tail Out, and No Tail refer to the relative relationship of the hexyl chain on the, in this example, thiophene moieties relative to the annulene ring;

FIG. 2 shows that representative structures of curved M10A, planar aromatics, and bicyclic planar aromatics offer differing degrees of torsional strain, which affects conjugation length in polymers comprising such units;

FIG. 3 are UV-vis (left) and photoluminescence (right) for the homopolymers of TMT (PTMT) (top) and TMT (bottom) series of compounds disclosed herein. Polymer absorption profiles are normalized relative to the lowest energy maxima. Excitation for each polymer occurred at the $\lambda_{max}$ of the individual polymers. Tail In (—), Tail Out (- - -), No Tail (• • •);

FIG. 4 is a UV-Vis spectrum of No Tail PTMT in $CHCl_3$ solution at room temperature;

FIG. 5 shows UV-vis (left) and photoluminescence (right) spectra for the PTMT-T (top) and TTMTT (bottom) series of compounds disclosed herein. Polymer absorption profiles are normalized relative to the lowest energy maxima. Excitation for each polymer occurred at the $\lambda_{max}$ of the individual polymers. Tail In (—), Tail Out (- - -), No Tail (• • •);

FIG. 6 shows UV-vis (left) and photoluminescence (right) data for the PTMT-B (top) and BTMTB (bottom) series. Polymer absorption profiles are normalized relative to the lowest energy maxima. Excitation for each polymer occurred at the $\lambda_{max}$ of the individual polymers. Tail In (—), Tail Out (- - -), No Tail (• • •);

FIG. 7 shows absorption spectra of PTMT-DPP series of compounds disclosed herein. Polymer absorption profiles are normalized relative to the lowest energy maxima. Tail In (—), Tail Out (- - -), No Tail (• • •);

FIG. 8 shows X-ray diffractograms of annealed films of P3HT (left) and Tail In PTMT-B (right); and FIG. 9 shows transistor characteristics of Tail Out PTMT-DPP in plots of $I_d$ VS. $V_d$ (left) and $I_{d0.5}$ vs. $V_g$ (right).

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

I. Torsional Influences within Disordered Organic Electronic Materials Based on Non-Benzenoid 1,6-methano[10]Annulene Rings The non-benzenoid moiety 1,6-methano[10]annulene (M10A) has been investigated previously as a candidate building block for semiconducting polymeric materials based on its unusual non-benzenoid aromaticity. Peart, P. A.; Tovar, J. D. Org. Lett. 2007, 9, 3041; Peart, P. A.; Repka, L. M.; Tovar, J. D. Eur. J. Org. Chem. 2008, 2193; Peart, P. A.; Tovar, J. D. Macromolecules 2009, 42, 4449; Peart, P. A.; Elbaz, G.; Tovar, J. D. Pure Appl. Chem. 2010, 82, 1045. This aromatic system was first synthesized by Vogel and Roth in 1964, Vogel, E.; Roth, H. D. Angew. Chem. 1964, 76, 145, and can be viewed as a valence isomer of the bisnorcaradiene motif present on substituted fullerenes, such as PC61BM. Hummelen, J. C., et al., J. Org. Chem. 1995, 60, 532-538. M10A offers lower oxidation potentials, increased effective conjugation lengths, and decreased bandgaps in polymers that contain it relative to benzenoid building blocks.

The bridged, curved structure of M10A potentially could frustrate interchain i-stacking, possibly leading to amorphous solid-state materials. Although seemingly counterintuitive, amorphous materials exhibit good device characteristics in thin films and result in enhanced processability due to a reduced tendency to experience π-stacking-driven aggregation in solution and reduced phase segregation in thin films. Sirringhaus, H. Adv. Mater. 2005, 17, 2411; Baek, N. S., et al., Chem. Mater. 2008, 20, 5734; Osaka, I.; Zhang, R.; Sauvé, G.; Smilgies, D.-M.; Kowalewski, T.; McCullough, R. D. J. Am. Chem. Soc. 2009, 131, 2521.

For high-throughput applications, such as inkjet printing, where undesired aggregation and precipitation are major factors, these properties are highly desired. In addition to these characteristics, the curved molecular geometry of M10A has the potential to reduce the steric clashes resulting from alkyl chains on neighboring aromatic rings. Accordingly, the presently disclosed subject matter discloses the use of M10A in extending conjugation length in alkylated conjugated polymers due to reduced annulene-alkyl torsional strain relative to other larger planar aromatic subunits. To this end, the presently disclosed subject matter describes the synthesis of M10A-based conjugated polymers and small molecule models having different alkyl chain orientations relative to the annulene core to probe the amount of steric relief granted by aromatics exhibiting a curved molecular geometry.

More particularly, the presently disclosed synthesis methods incorporate M10A and a variety of aromatic moieties, such as benzothiadiazole and diketopyrrolopyrrole. Each series consists of a "Tail In" and a "Tail Out" version having hexyl chains attached to the 3- or 4-positions, respectively, of the aromatic moieties directly attached to the 2,7-positions of 1,6-methano[10]annulene. For illustrative purposes, shown in FIG. 1 are representative "Tail In" and "Tail Out" versions of 2,7-bis(3-hexyl-2-thienyl)-1,6-methano[10]annulenes, as well as a "No Tail" version having no hexyl groups.

Regioregular copolymers prepared from these subunits showed differences in torsional interactions as determined by the relative positions of the hexyl chains. The electronic properties of polymers and small molecules were characterized by UV-vis and photoluminescence spectroscopy, and the polymers were characterized by $^1$H NMR and gel permeation chromatography. Cyclic voltammetry was used to investigate their solution electrochemistry. A clear correlation between electronic properties and hexyl chain regiochemistry was observed. Without wishing to be bound to any one particular theory, the implications of these correlations are that curved aromatics can be used to influence and interrogate torsional interactions along the backbone of conjugated polymers, while promoting solubility and disordered π-stacking in the solid state.

More particularly, the presently disclosed subject matter provides a compound of Formula (I) or Formula (II):

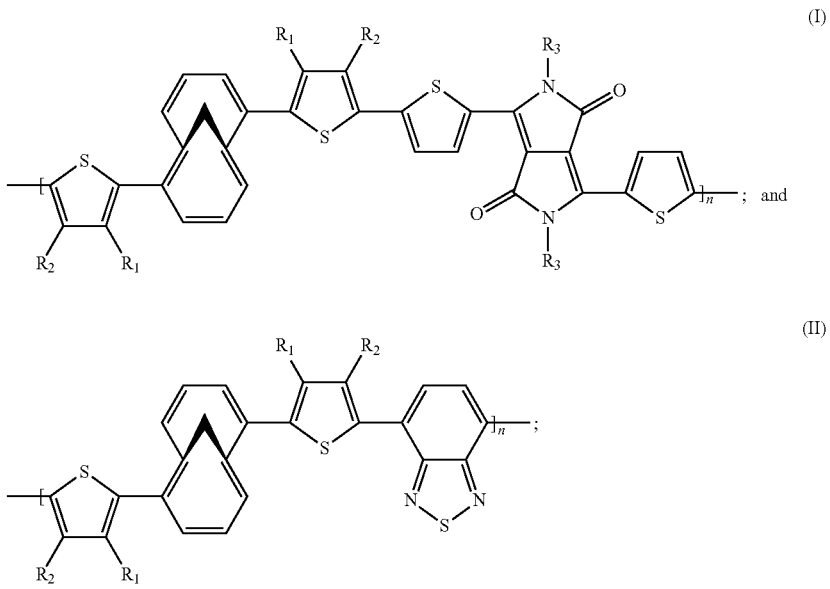

wherein: n is an integer selected from the group consisting of 1 to 150; and $R_1$, $R_2$, and $R_3$ are each independently selected from the group consisting of H and $C_6$-$C_{20}$ linear or branched alkyl.

In some embodiments, $R_3$ is $C_8H_{12}$ and the compound of Formula (I) is selected from the group consisting of:

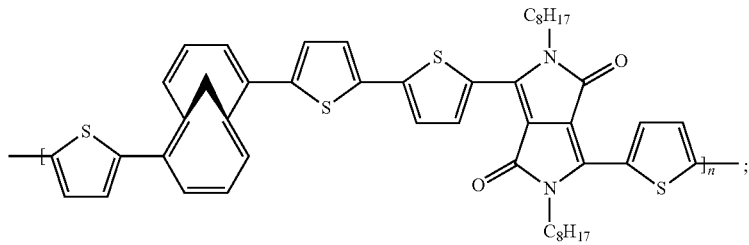

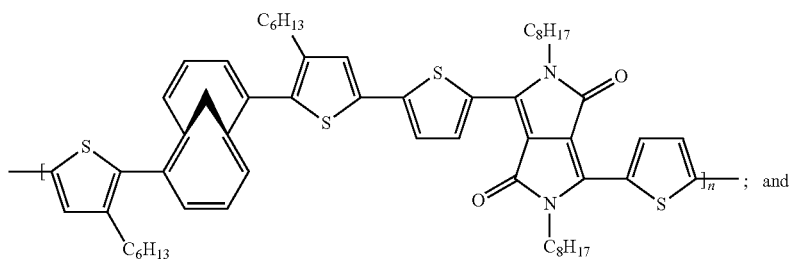

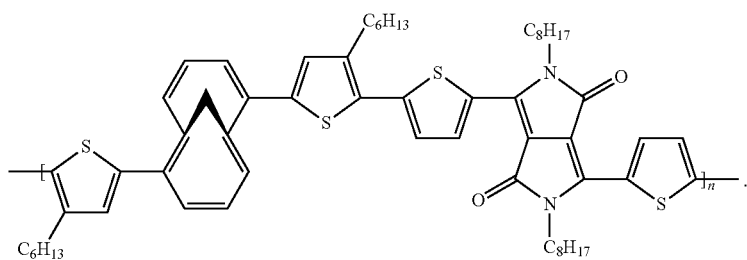

In particular embodiments, the compound of Formula (II) is selected from the group consisting of:

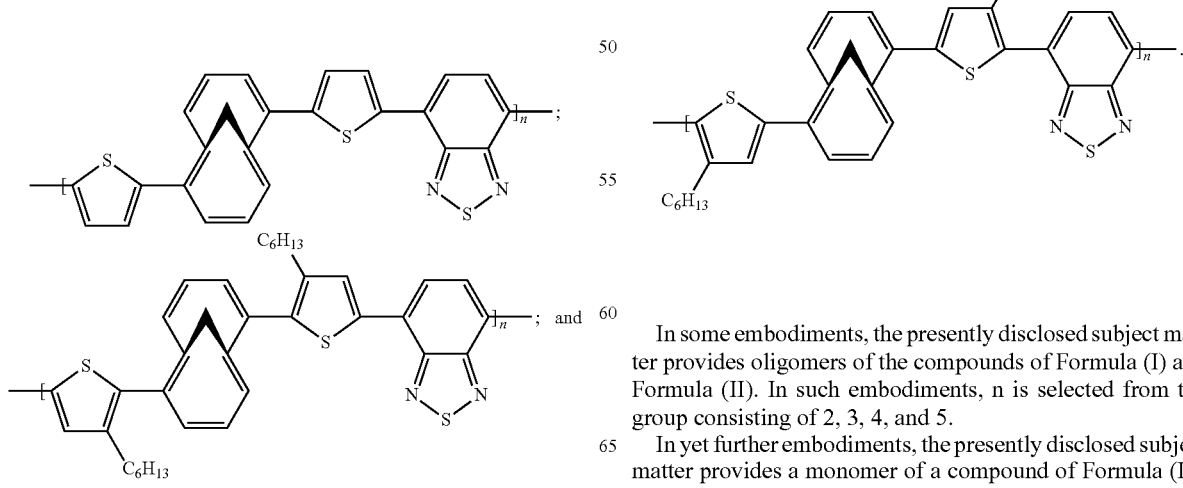

In some embodiments, the presently disclosed subject matter provides oligomers of the compounds of Formula (I) and Formula (II). In such embodiments, n is selected from the group consisting of 2, 3, 4, and 5.

In yet further embodiments, the presently disclosed subject matter provides a monomer of a compound of Formula (II), wherein the monomer is a compound of Formula (III):

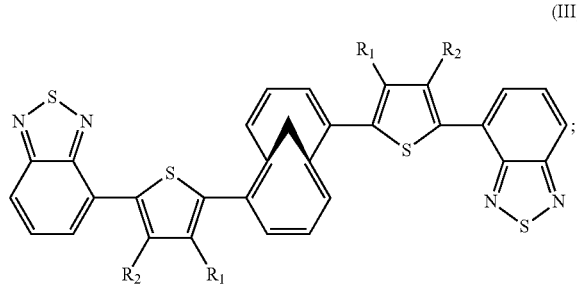

(III)

wherein $R_1$ and $R_2$ are as defined herein above.

In particular embodiments, the compound of Formula (III) is selected from the group consisting of:

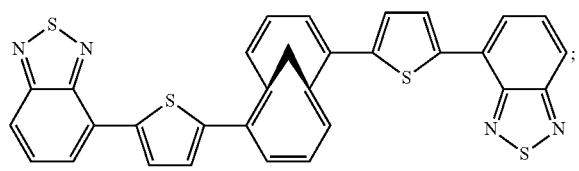

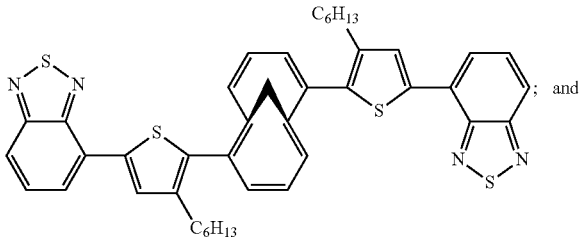

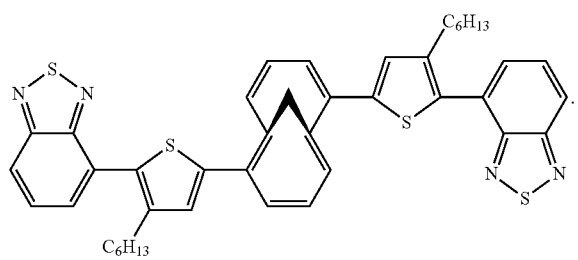

In some embodiments, the presently disclosed subject matter provides a film comprising a compound of Formula (I) or Formula (II):

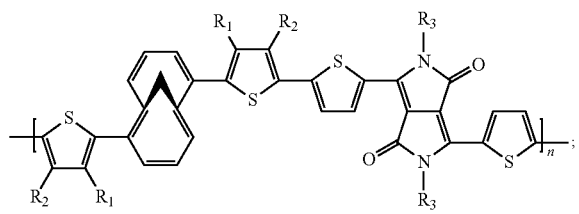

(I)

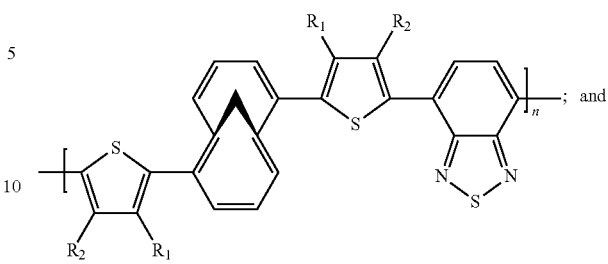

(II)

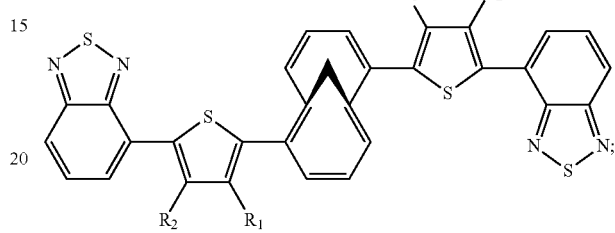

wherein: n is an integer selected from the group consisting of 1 to 150; and $R_1$, $R_2$, and, $R_3$ are each independently selected from the group consisting of H and $C_6$-$C_{20}$ linear or branched alkyl.

In particular embodiments, the film further comprises a blend of a compound of Formula (I) or Formula (II) and one or more of an electron donating material and an electron accepting material. In certain embodiments, the electron accepting material comprises a fullerene. In more particular embodiments, the fullerene comprises [6,6]-phenyl-$C_{61}$-butyric acid methyl ester (PCBM). In certain embodiments, the electron donating material is selected from the group consisting of poly(3-hexyl thiophene) (P3HT) and 2-methoxy-5-(2'-ethylhexyloxy)-p-phenylene vinylene (MEH-PPV).

In other embodiments, the presently disclosed subject matter provides a device comprising the film of compounds of Formula (I) or Formula (II). In representative embodiments, device comprises a bulk heterojunction organic photovoltaic (BHJ-OPV) device. In other embodiments, the device comprises a layered device, in which at least one of a p-channel layer or a n-channel layer comprises a compound of Formula (I) or Formula (II).

Accordingly, the presently disclosed subject matter includes a device comprising a compound or film of Formula (I) or Formula (II):

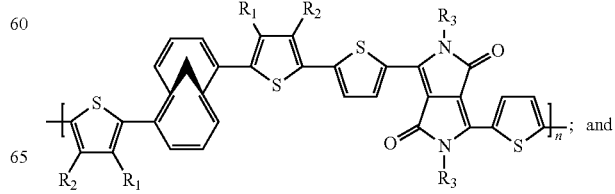

(I)

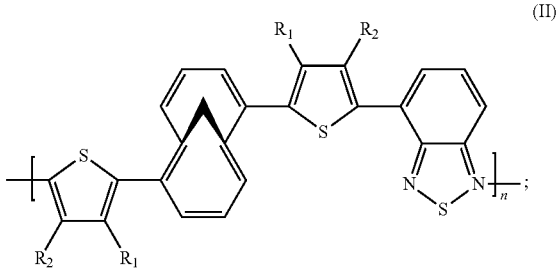

wherein: n is an integer selected from the group consisting of 1 to 150; and $R_1$, $R_2$, and, $R_3$ are each independently selected from the group consisting of H and $C_6$-$C_{20}$ linear or branched alkyl.

Accordingly, in some embodiments, the device can be an organic semiconductor, which in some embodiments, can be light emitting, charge transporting, or energy harvesting. In other embodiments, the device is selected from the group consisting of a thermoelectric device and an organic photovoltaic device.

In some embodiments, the presently disclosed subject matter includes a field-effect transistor comprising a compound of Formula (I) or Formula (II). The field-effect transistor generally includes, at least, a substrate, a semiconductor layer formed through a coating process, a source electrode, and a drain electrode. As used herein, a "field-effect transistor" is a transistor that uses an electric field to control the shape and hence the conductivity of a channel of one type of charge carrier in a semiconductor material. More particularly, the semiconductor layer of the field-effect transistor can include a compound of Formula (I) or Formula (II). The field-effect transistor can be used in electronic devices and photoelectronic devices including, but not limited to, display elements, electronic tags, electromagnetic sensors, pressure sensors, and the like.

In certain embodiments, the device comprises an organic field-effect transistor. As used herein, an "organic field-effect transistor" (OFET) is a field-effect transistor comprising an organic semiconductor in its channel. In some embodiments, the OFET can be an organic light-emitting field-effect transistor (OLET).

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) or Formula (II) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

The description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, an alkyl group or heteroalkyl group is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl)

hydrocarbon radicals derived from a hydrocarbon moiety containing between one and twenty carbon atoms by removal of a single hydrogen atom. In more particular embodiments, "alkyl" refers to $C_6$-$C_{20}$ linear or branched alkyl, in which the alkyl group has about 6 to about 20 carbon atoms, including, 6, 7, 8, 9, 10, 11, 12, 13, 14, 15, 16, 17, 18, 19, or 20 carbon atoms.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

As used herein, the term "alkyl" also encompasses heteroalkyl moieties. The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{2S}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, 0-$CH_3$, -0-$CH_2$—$CH_3$, and —CN. Up to two or three heteroatoms may be consecutive, such as, for example, —$CH_2$—NH—O$CH_3$ and —$CH_2$—O—Si($CH_3$)$_3$.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Synthesis and Characterization of Disordered Organic Electronic Materials Based on Non-Benzenoid 1,6-Methano[10]annulene Rings Conjugated polymers and small molecules containing the nonplanar aromatic 1,6-methano[10]annulene were synthesized in an effort to understand how torsional differences between planar and nonplanar π-electron components influence the electronic properties of π-conjugated materials. The polymers and small molecule model systems contain aromatic subunits, such as thiophene, diketopyrrolopyrrole, and 2,1,3-benzothiadiazole, leading to electron donor and donor-acceptor polymers.

The curved geometry of 1,6-methano[10]annulene can lead to reduced local torsional strain in semiconducting polymers relative to large planar aromatics, potentially increasing intrapolymer conjugation. The relative amount of effective conjugation length increase granted by the annulene in each system of regioisomers was interrogated through the use of UV-vis and photoluminescence spectroscopy and electrochemistry, and it was found that 1,6-methano[10]annulene relieves some torsional strain associated with solubilizing alkyl chains clashing with aromatic rings along the polymer backbone. The polymers also were found to be highly disordered in thin films, yet still provided reasonable hole mobilities (ca. $10^{-4}$ $cm^2/(V\,s)$) in organic field-effect transistor (OFET) devices. These results suggest that methano[10]annulene or other curved aromatics may prove useful in the development of organic electronics.

Synthesis of Polymers and Model Systems.

Several polymers and molecular models were synthesized, built upon the aforementioned Tail In, Tail Out, and No Tail thiophene-M10A-thiophene (TMT) subunits shown in FIG. 1. The orientation of the hexyl chains in the polymers should change little as far as electron donation into the aromatic backbone of the polymer, but is expected to dramatically alter the torsional influences (FIG. 2) involved in maintaining an extended effective conjugation length (ECL). For example, the curved nature of M10A should alleviate the steric clashing with solubilizing groups (the substituent group "R" in FIG. 2) relative to larger or more planar aromatic subunits. These TMT monomers were synthesized by palladium catalyzed cross-couplings between 2,7-dibromo-1,6-methano[10]annulene and various 2-(tributylstannyl)-thiophenes to afford the Tail In, Tail Out, and No Tail TMT products (Scheme 1).

Scheme 1. Synthesis of Thiophene-M10A-Thiophene (TMT) Monomers.

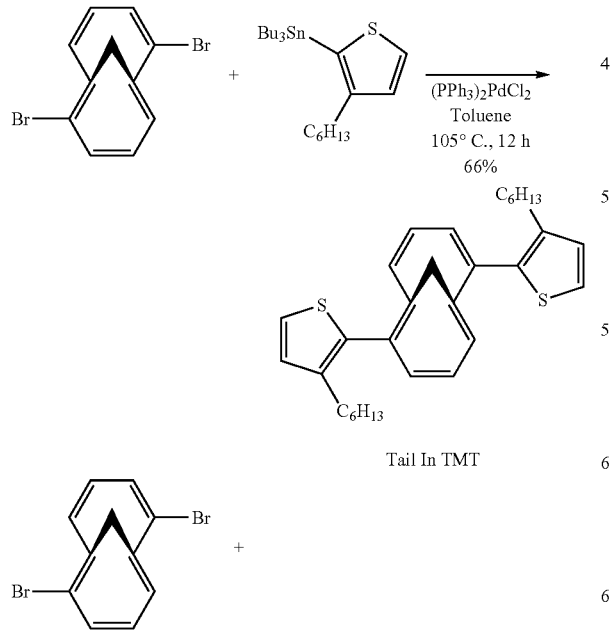

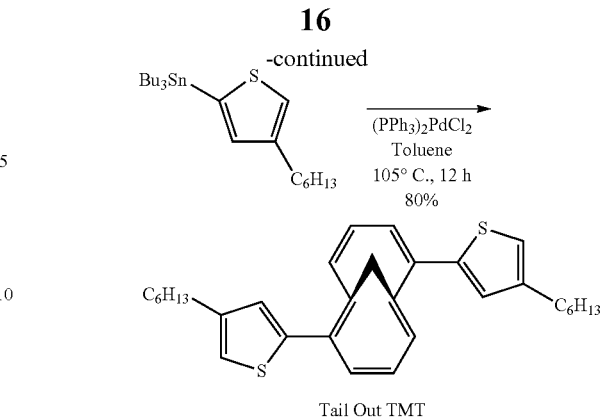

Tail Out TMT

Neidlein established the utility of Pd-catalyzed cross-coupling on M10A cores for optical materials, Bryant-Friedrich, A. C.; Neidlein, R. Helv. Chim. Acta 1997, 80, 128; Bryant-Friedrich, A. C.; Neidlein, R. Helv. Chim. Acta 1997, 80, 1639, and this method subsequently was used for electropolymerizable molecules. Peart, P. A.; Tovar, J. D. Org. Lett. 2007, 9, 3041. Tail In and Tail Out TMT were purified via column chromatography, and the No Tail variant was purified by recrystallization according to previously reported procedures. Peart, P. A.; Repka, L. M.; Tovar, J. D. Eur. J. Org. Chem. 2008, 2193.

The TMT molecules are readily stannylated at the thienyl α-positions by lithiation and quenching with tributylstannyl chloride (Scheme 2).

Scheme 2. Stannylation and Bromination of the TMT Monomers.

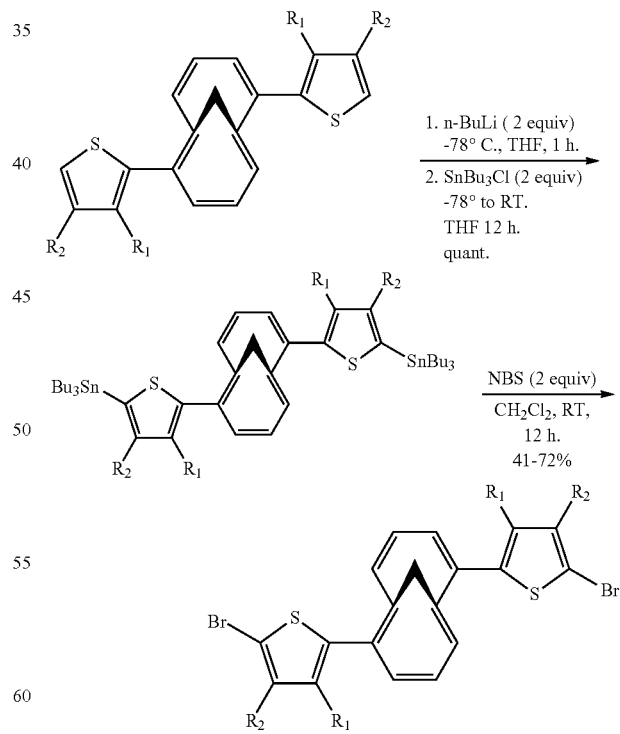

Tail In: $R_1$ = hexyl, $R_2$ = H; Tail Out: $R_1$ = H, $R_2$ = hexyl; No Tail: $R_1$ = $R_2$ = H.

These reactions proceed in high yields, but the excess tin electrophile required to drive the reactions to completion makes final purification difficult. The bis(tributylstannyl)-

TMT compounds were carried on to the next reaction as isolated, with NMR integrations being used to estimate purity for accurate stoichiometry in subsequent reactions. Nevertheless, the lack of analytical purity for the stannylated comonomers led to unavoidable stoichiometry imbalances that could have potentially impacted the observed molecular weights. The TMT molecules also are easily brominated at the same α-thienyl positions with NBS in dichloromethane. The dibromo-TMT compounds are purifiable by column chromatography and are isolated in acceptable yields. The distannane and the dibromide precursors are set up to perform a variety of transition-metal-catalyzed crosscouplings to access either polymers (Scheme 3) or small molecules (see Scheme 4 herein below).

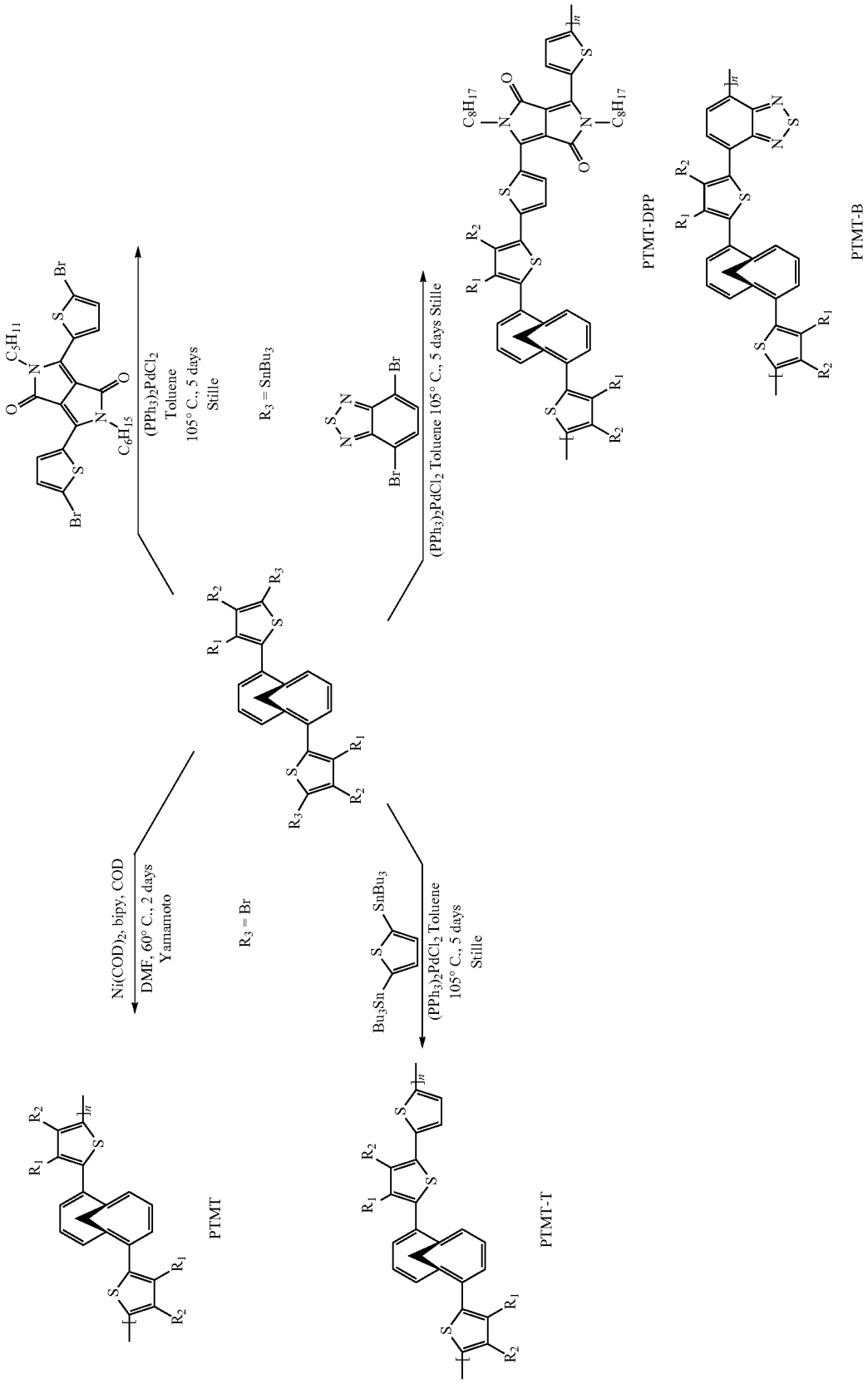
Scheme 3. Polymer Syntheses from TMT Monomers.
Tail In: R₁ = hexyl, R₂ = H; Tail Out: R₁ = H, R₂ = hexyl; No Tail: R₁ = R₂ = H.

Homopolymers of the TMT subunits (PTMT, Scheme 3) were synthesized by Yamamoto reductive couplings of the dibromo-TMT units using a bipyridyl-nickel complex formed in situ from Ni(COD)$_2$ and 2,2'-bipyridine (Scheme 3). The polymerization of the dibromo-TMT monomers proceeded by heating to 60° C. for 2-4 days in dry DMF. The PTMT-T series was synthesized from the copolymerization of the dibromo-TMT monomers with 2,5-bis(tributylstannyl)-thiophene via Stille couplings. The standard Stille coupling procedure was modified by addition of copper(I) iodide to activate the thienyl bromide toward oxidative addition, as well as cesium fluoride to activate the (tributylstannyl)thiophene toward transmetalation. Mee, S. P. H., et al., Angew. Chem., Int. Ed. 2004, 43, 1132.

PTMTs and PTMT-Ts were precipitated from methanol and filtered. The Tail In and Tail Out PTMTs and PTMT-Ts were soluble in common organic solvents, but the No Tail polymers were rather insoluble. The PTMT-B and PTMT-DPP polymer series were synthesized from the bis(tributylstannyl)-TMT monomers by Stille coupling with the electron-poor dibromides of 2,1,3-benzothiadiazole, Karikomi, M., et al., J. Am. Chem. Soc. 1995, 117, 6791-6792, and bis(thienyl)diketopyrrolopyrrole. Bijleveld, J. C., et al., J. Am. Chem. Soc. 2009, 131, 16616; Woo, C. H., et al., J. Am. Chem. Soc. 2010, 132, 15547.

The PTMT-B and PTMT-DPP syntheses disclosed herein use enhanced Stille coupling procedures similar to those used in the PTMT-T synthesis, but without the catalytic CuI to activate the aryl bromide, because electron-deficient aromatics typically undergo rapid oxidative addition. The PTMT-B and PTMT-DPP series were precipitated directly into methanol and filtered to obtain final product. All variants were soluble in chlorinated organic solvents, although the No Tail polymers seemed to be less soluble in the same solvents than the tailed counterparts. All polymers were analyzed by gel permeation chromatography to determine their approximate molecular weights relative to polystyrene standards. The values were not corrected and are assumed to be overestimates due to the rod-like structure of the polymers and the possibility of aggregation leading to exaggerated molecular weight measurements. Holdcroft, S. J. Polym. Sci., Part B: Polym. Phys. 1991, 29, 1585-1588.

TABLE 1

Polymer Molecular Weight Data Obtained by Gel Permeation Chromatography

| series | orientation | $M_n$ (g/mol) | $M_w$ (g/mol) | PDI[a] | $DP_n$[b] |
|---|---|---|---|---|---|
| PTMT | Tail In | 3800 | 6200 | 1.61 | 8 |
| | Tail Out | 2400 | 4900 | 2.05 | 5 |
| | No Tail | insoluble in THF | | | |
| PTMT-T | Tail In | 3600 | 11 100 | 3.11 | 6 |
| | Tail Out | 5700 | 15 000 | 2.63 | 10 |
| | No Tail | insoluble in THF | | | |
| PTMT-B | Tail In | 3800 | 7800 | 2.05 | 6 |
| | Tail Out | 3000 | 7700 | 2.57 | 9 |
| | No Tail | insoluble in THF | | | |
| PTMT-DPP | Tail In | 3200 | 5500 | 1.72 | 3 |
| | Tail Out | 3000 | 4700 | 1.58 | 6 |
| | No Tail | insoluble in THF | | | |

[a]Polydispersity index (PDI) is calculated as $M_w/M_n$.
[b]Degree of polymerization (DP$_n$) is calculated as $M_n$/repeat unit formula weight.

In some cases, however, the molecular weights were low. Without being bound to any one particular theory, it is thought that the number of individual π-conjugated components in the polymer repeat units is sufficient to yield polymers capable of maintaining the inherent effective conjugation length (that usually comprise approximately 10 aromatic rings). Wohlgenannt, M., et al., Phys. Rev. B 2004, 69, 241204(R). The solvent used for this particular chromatography setup was THF at ambient temperature, which did not allow analysis of the No Tail polymers within any of the polymer series due to severe insolubility even after extended sonication and heating. The No Tail polymers, however, were sparingly soluble in o-dichlorobenzene-d$_4$, thereby allowing for $^1$H NMR characterization. Peak broadening in the NMR spectrum indicates degrees of polymerization comparable to those of the Tail In and Tail Out within the same series.

Oligomeric model systems were synthesized to mimic the polymeric series in structure and hexyl chain orientation. These small molecule models were designed to help elucidate torsional interactions without any dependence on molecular weight differences. As used herein, the term "oligomer" refers to a molecule comprising a few monomer units, in contrast to a polymer that, at least in principle, can comprise an unlimited number of monomers. Dimers (two monomer units), trimers (three monomer units), tetramers (four monomer units), pentamers (five monomer units), hexamers (six monomer units), and heptamers (seven monomer units) are non-limiting examples of oligomers.

The TTMTT and BTMTB systems are synthesized by Stille coupling (Scheme 4) by end-capping the TMT monomer with a thienyl or benzothiadiazole group, respectively. The molecular models were purified by column chromatography and characterized by $^1$H and $^{13}$C NMR, as well as HR-MS.

Scheme 4. Syntheses of TTMTT (top) and BTMTB (bottom) Small Molecule Model Systems.

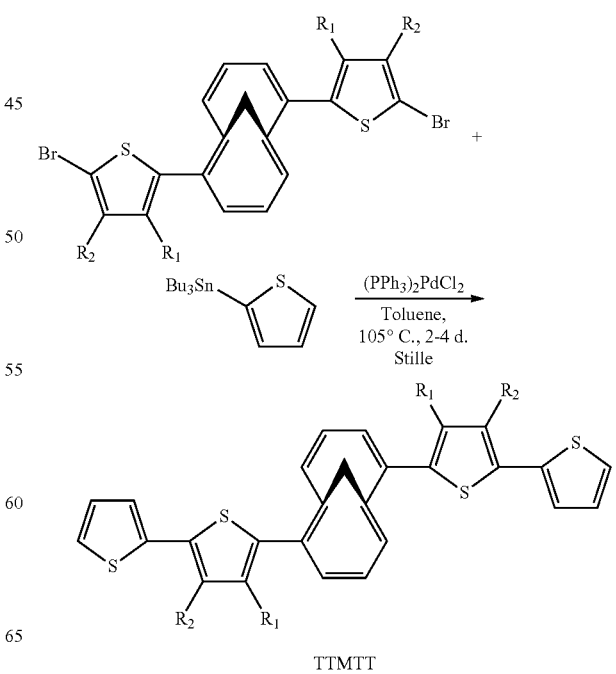

TTMTT

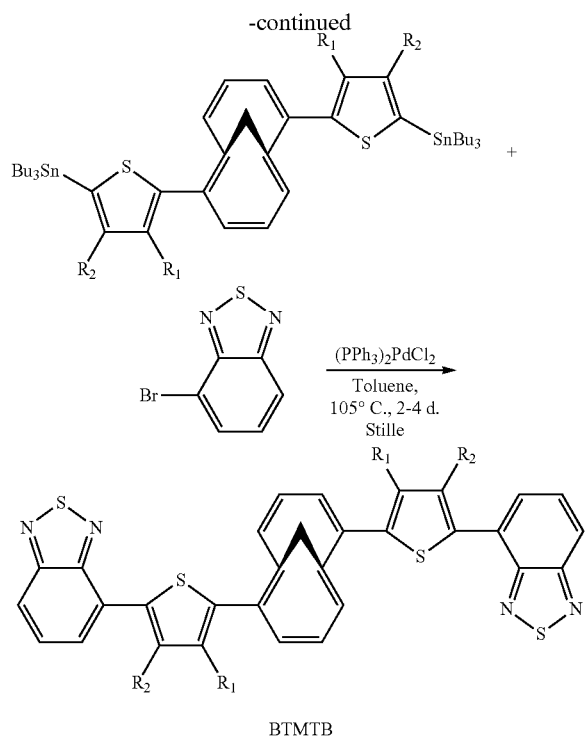

BTMTB

Tail In: $R_1$ = hexyl, $R_2$ = H; Tail Out: $R_1$ = H, $R_2$ = hexyl; No Tail: $R_1$ = $R_2$ = H.

Electronic Absorption and Photoluminescence.

UV-vis spectrophotometry was used to determine the relative degree of electronic delocalization along each polymer chain and within the small molecule models. For a polymer with a specific π-conjugated repeating unit, a longer effective conjugation length leads to lower energy absorption, so any forces that may cause the aromatic rings to deviate dramatically from planarity should be apparent in the electronic absorption spectrum by way of hypsochromic shifts in the onsets and/or maxima of absorption to higher energy. A torsional deviation of around 30°-40° from coplanarity has been shown computationally to effectively interrupt conjugation. Brédas, J. L. J. Chem. Phys. 1985, 82, 3809.

TABLE 2

UV - vis and Photoluminescence Data for Polymers and Molecular Models[a]

| series | orientation | $\lambda_{max}$ (nm) | onset (nm) | $PL_{max}$ (nm) | Stokes shift (nm) |
|---|---|---|---|---|---|
| PTMT | Tail In | 430 | 520 | 546 | 116 |
| | Tail Out | 418 | 513 | 551 | 133 |
| | No Tail | 468 | 540 | 601 | 133 |
| PTMT-T | Tail In | 422 | 540 | 546 | 124 |
| | Tail Out | 435 | 575 | 572 | 137 |
| | No Tail | 455 | 550 | 560 | 105 |
| PTMT-B | Tail In | 512 | 595 | 622 | 110 |
| | Tail Out | 478 | 580 | 619 | 141 |
| | No Tail | 520 | 610 | 621 | 101 |
| PTMT-DPP | Tail In | 637 | 810 | | |
| | Tail Out | 636 | 810 | | |
| | No Tail | 644 | 803 | | |
| TMT | Tail In | 365 | 438 | 499 | 134 |
| | Tail Out | 383 | 460 | 571 | 188 |
| | No Tail | 375 | 467 | 512 | 137 |
| TTMTT | Tail In | 389 | 490 | 530 | 141 |
| | Tail Out | 414 | 511 | 549 | 135 |
| | No Tail | 417 | 510 | 550 | 133 |

TABLE 2-continued

UV - vis and Photoluminescence Data for Polymers and Molecular Models[a]

| series | orientation | $\lambda_{max}$ (nm) | onset (nm) | $PL_{max}$ (nm) | Stokes shift (nm) |
|---|---|---|---|---|---|
| BTMTB | Tail In | 446 | 576 | 611 | 165 |
| | Tail Out | 425 | 560 | 599 | 174 |
| | No Tail | 509 | 598 | 627 | 118 |

[a]All spectra recorded in chloroform at ambient temperature. Onset was determined to be the wavelength at which the absorption reached 5% above the baseline.

Tail In PTMT has a slightly red-shifted absorption maximum and onset compared to Tail Out PTMT (12 nm and 7 nm, respectively, FIG. 3). The thiophene linkages within this series can be viewed as models of head-to-head (HH) and tail-to-tail (TT) couplings, as defined generally by McCullough for P3ATs. McCullough, R. D. Adv. Mater. 1998, 10, 93.

The bithiophene units in the Tail Out configuration correspond to a HH coupling, a torsional defect known to result in conjugation-breaking rotation out of coplanarity. The Tail In structure corresponds to a TT defect, but, again without wishing to be bound to any one particular theory, it is thought that the extent to which this TT defect affects the conjugation is mitigated by the presence of the curved M10A ring. No Tail PTMT appears to show an even further red-shifted absorption maximum and onset (FIG. 4) and can be interpreted as a baseline of dihedral orientations inherent to the polymer backbone without alkyl chain influence. No Tail PTMT, however, aggregates strongly in solution, leading to excessive scattering and a nonzero baseline in the absorption spectrum, so the observed values also could reflect planarized and/or aggregate structures.

The photoluminescence spectra of the PTMT series show similar emission maxima, but different Stokes shifts (106 nm Tail In, 133 nm Tail Out). The larger Stokes shift for the Tail Out polymer suggests it must undergo more reorganization in the excited state to reach a more planar lower energy structure necessary to better stabilize the excited state. This observation follows from the more sterically demanding HH linkage present in Tail Out PTMT. The TMT monomers show the opposite trend of the PTMT series in the absorption spectrum (FIG. 3). Tail Out TMT shows a lower energy onset and absorption maximum compared to the Tail In (by 18 and 22 nm, respectively). This trend is expected due to the lack of significant steric interference acting on the hexyl chain of the Tail Out TMT compared to the presence of the annulene adjacent to the hexyl group for Tail In TMT.

The photoluminescence spectrum also reflects these differences, with an 18-nm shift in the emission maxima from Tail In to Tail Out. Given the lack of sterically demanding groups adjacent to the portion of the thiophene ring furthest from the annulene, it is not surprising that No Tail TMT shows similar spectral behavior to Tail Out TMT, with both showing basically identical absorption and emission profiles. The PTMT-T series shows the opposite trend of PTMT (FIG. 5); the absorption maximum and onset of the Tail Out configuration are lower in energy than the Tail In (13 nm and 35 nm, respectively). The PTMT-T series assesses the difference between adjacent hexylannulene (large, curved) and hexylthiophene (small, planar) torsional interactions. In this particular case, the geometry of the annulene is not enough to make up for the size difference between the thiophene and [10]-annulene. When the hexyl chains are directed toward the annulene, some degree of freedom exists for the solubilizing chain that can lead to a reduction in torsional angle, as evidenced by the PTMT series, but not as much as is available when the hexyl chain is directed toward a relatively nonsterically demanding thiophene ring.

The photoluminescence of the PTMT-T series shows the same trend as the TMT model series; the Tail In shows a higher energy emission, but smaller Stokes shift than the Tail Out. The more conjugated Tail Out polymer has a lower energy emission maximum than does the Tail In. The Stokes shifts indicate that less energy is needed to relax the excited state of the Tail In polymer due to it preexisting in a relatively restricted conformation compared to the Tail Out analogue and therefore cannot achieve a comparable extent of coplanarity in the excited state. The No Tail polymer shows the furthest red shift in the absorption and the lowest Stokes shift, giving a baseline of coplanarity and extended conjugation for this polymer series due to the inherent hexyl-thienyl interactions.

The TTMTT molecular models show the same trends as their PTMT-T counterparts, with Tail Out TTMTT exhibiting lower energy absorption features than Tail In TTMTT (25-nm maximum and 21-nm onset red-shifted differences). The rationale invoked for the TMT and PTMT-T series also is valid here: the terminal thiophenes of these models present, in essence, the same steric environment as the thiophene comonomer subunit of the PTMT-T series, giving the Tail Out configuration the opportunity to achieve a more coplanar conformation. The photoluminescence of the TTMTT models also follows the aforementioned trends of the PTMT-T series, exhibiting a red-shifted Tail Out emission maximum. The Stokes shift of the TTMTT series shows a greater shift for the Tail In relative to the Tail Out model (141 nm and 135 nm, respectively). Without wishing to be bound to any one particular theory, this observation supports the premise that the terminal thiophenes of the TTMTT series present a similar steric environment to the thiophene comonomer subunits in PTMTT, without the formation of an HH defect commonly seen in regioirregular polythiophenes. The greater Stokes shift for Tail In TTMTT suggests that the Tail In system pre-exists in a relatively restricted conformation, much like the parent polymer.

No Tail TTMTT follows the same trend as No Tail PTMT-T: red-shifted absorption and the smallest Stokes shift of the series, and the reasoning remains the same as for the polymer series. With an assessment of how solubilizing hexyl groups influence torsional properties of thiophene-based conjugated polymers containing the nonplanar M10A segment, other polymers with broader absorption across the visible spectrum were investigated. The PTMT-B series interrogates the difference between hexyl-annulene and hexyl-benzothiadiazole interactions. This characteristic differs in several ways from the PTMT-T series; the enzothiadiazole core is bicyclic and presents a larger surface to interfere with the adjacent hexyl chains, and the electron-poor nature of benzothiadiazole creates a donor-acceptor system in the polymer chain that significantly lowers the optical band gap.

As seen in FIG. 6, the Tail In polymer has a lower energy absorption maximum and onset than the Tail Out (by 34 nm and 15 nm, respectively). The lone pairs on the heteroatoms forming the bicyclic ring system, as well as the greater bond angles in the 6-membered ring versus a 5-membered thiophene may have an effect on the ECL by inducing significant torsional strain on the polymer backbone. These effects add up to allow the Tail In polymer, on average, to reach a more planar and conjugated state than Tail Out PTMT-B. The photoluminescence data follow the trends previously seen in the PTMT and PTMT-T series. The emission maxima for all three polymers are within 3 nm and the emission profiles overlap nearly perfectly, but the Stokes shifts follow similar trends (124 nm Tail In, 137 nm Tail Out).

Considering the alternating donor-acceptor structure of the polymers and the tendency for such systems to undergo intramolecular charge transfer, it is possible that the excited states of the polymers are able to overcome steric interactions to better adopt comparably planar structures that can emit photons of similar energy. Because electronic transitions between states happen prior to nuclear reorganization, all three polymers could emit from a comparably planarized fluorophore and then relax back to their ground state conformations.

An alternative explanation, whereby the similarity in PL wavelengths in the polymers with stronger acceptors could originate from twisted intramolecular charge transfer (TICT) states, has been suggested. Grabowski, A. R.; Rotkiewicz, K. Chem. Rev. 2003, 103, 3899-4032. Although this explanation is a possibility, the polymer dispersities and the lack of strong vibronic features in the PL spectra would preclude the unambiguous assessment of any spectral attenuation as a function of molecular solvent parameters or other definitive spectroscopic characterizations of these states that would be necessary to suggest TICT over other electronic processes.

No Tail PTMT-B follows a trend similar to the previous series: red-shifted absorption maximum and onset and lower Stokes shift compared to the Tail Out polymer, but relatively similar values compared to Tail In PTMT-B. The BTMTB models show similar absorption trends to the respective PTMT-B polymers. Although the multiple features in the absorption profile make it difficult to pick definitive absorption maxima, the onset difference in this model series clearly shows the Tail In configuration is red-shifted 16 nm from the onset of the Tail Out. This property differs from the TTMTT series where the terminal aromatic rings could adopt a conformation that contributed to the delocalized electronic system without inducing steric strain. The size and bond angles of benzothiadiazole restrict the degree to which the terminal rings can adopt coplanar structures, resulting in the Tail In model having a lower energy onset of absorption. Thus, the hexyl-annulene interactions may be more amenable to coplanar conformations than hexyl-benzothiadiazole interactions.

In an effort to study even more broadly absorbing, low-band-gap polymers, the PTMT-DPP series was designed and synthesized. The PTMT-DPP series shows an interesting absorption trend (FIG. 7) not yet demonstrated in the other polymer and oligomeric model systems reported here. The lowest energy absorption maxima and onsets of all three polymers in the series are essentially identical. This observation is likely due to the domination of the low-energy portion of the spectrum by a charge transfer band resulting from the stronger donor-acceptor nature of the DPP-containing polymers. Although the molecular weights are very small for the DPP-containing polymers, they should be of sufficient length to accommodate the inherent ECL. Prior work with carbazole-DPP alternating copolymers has shown that very little optical variation ($\lambda_{max}$ ranging from 630 nm to 642 nm in dilute $CHCl_3$ solutions) arising from molecular weight differences (between 4,000 and 30,000 g/mol) is observed even with the inclusion of the stronger carbazole electron donor unit. Zou, Y., et al., Macromolecules 2009, 42, 6361.

Features present at higher energies reveal a trend similar to that of the PTMT-T series. The local maxima occur at 403 nm, 416 nm, and 434 nm for the Tail In, Tail Out, and No Tail polymers, respectively. The PTMT-T and PTMT-DPP series have a similar portion of repeat unit that could influence the high-energy section of the spectrum. The reasoning for this trend is similar to that for the PTMT-T series, as well: because a 2,5-disubstituted thiophene is adjacent to the hexyl-substituted thiophenes of the TMT core, the Tail Out configuration has the freedom to adopt a planar conformation without the restricting influence of a directly adjacent larger aromatic group. The PTMT-DPP series is not photoluminescent.

Electrochemistry.

Each of the polymer and small molecule systems was studied by cyclic voltammetry (CV) to determine the HOMO energy. After measurement of the onset of oxidation and calculation of the HOMO level, the previously measured optical bandgap could be applied to obtain the LUMO energy. The general trend extracted from the data that across all polymers and molecular models, the Tail Out systems have an earlier onset of oxidation than do the Tail In of similar composition. The difference between them is relatively small, however, and may be an artifact of the complex interplay of surface effects, electrolyte interactions, solution capacitance, and the like, that can influence solution cyclic voltammetry. What seems to be a bigger difference than the subtle changes in the HOMO level is the change in the LUMO for each polymer and small molecule series (except the PTMT-T series). Attempts to perform cathodic CV did not yield results, despite the electron-accepting nature of the DPP subunit.

TABLE 3

Electrochemical Data for All Polymers and Small Molecule Systems Was Measured by Cyclic Voltammetry, and the HOMO Level Is Reported from Vacuum Using Fc/Fc+ as an External Standard;[a] HOMO Energy and the Optical Bandgap ($E_g$) Were Used to Calculate the LUMO Level

| SERIES | ORIENTATION | $E_{1/2}$ (MV) | ONSET (MV) | HOMO (EV) | LUMO (EV) | $E_G$ (EV) |
|---|---|---|---|---|---|---|
| PTMT | TAIL IN | 812 | 670 | −5.22 | −2.83 | 2.39 |
|  | TAIL OUT | 667 | 540 | −5.09 | −2.67 | 2.42 |
|  | NO TAIL | 635 | 540 | −5.09 | −2.79 | 2.30 |
| PTMT-T | TAIL IN | 687 | 551 | −5.09 | −2.80 | 2.29 |
|  | TAIL OUT | 632 | 474 | −5.01 | −2.86 | 2.15 |
|  | NO TAIL | 617 | 495 | −5.03 | −2.77 | 2.26 |
| PTMT-B | TAIL IN | 786 | 650 | −5.20 | −3.11 | 2.09 |
|  | TAIL OUT | 739 | 620 | −5.17 | −3.03 | 2.14 |
|  | NO TAIL | 742 | 620 | −5.17 | −3.14 | 2.03 |
| PTMT-DPP | TAIL IN | 705 | 490 | −4.98 | −3.45 | 1.53 |
|  | TAIL OUT | 696 | 460 | −4.95 | −3.42 | 1.53 |
|  | NO TAIL | 663 | 490 | −4.98 | −3.44 | 1.54 |
| TTMTT | TAIL IN | 808 | 678 | −5.18 | −2.65 | 2.53 |
|  | TAIL OUT | 811 | 649 | −5.15 | −2.73 | 2.42 |
|  | NO TAIL | 796 | 664 | −5.16 | −2.73 | 2.43 |
| BTMTB | TAIL IN | 925 | 771 | −5.27 | −3.12 | 2.15 |
|  | TAIL OUT | 875 | 718 | −5.22 | −3.01 | 2.21 |
|  | NO TAIL | 773 | 667 | −5.60 | −3.53 | 2.07 |

[a]Pommerehne, J., et al., J. Adv. Mater. 1995, 7, 551.

X-Ray Diffraction of Annealed Polymer Films.

X-ray diffraction analysis was used to determine if conjugated polymers containing 1,6-methano[10]annulene would form disordered aggregates when subjected to standard solution processing conditions. These conditions included drop-cast films of polymers and blends of electron-donor polymers and electron-accepting fullerenes to simulate common bulk heterojunction organic photovoltaic device compositions (BHJ-OPV). Brabec, C. J., Dyakonov, V., Scherf, U., Eds.; Organic Photovoltaics; Wiley-VCH: New York, 2008.

Films of P3HT, each previously described polymer, and a PTMTB:PCBM blend (1:1 by weight), wherein PCBM is [6,6]-phenyl-$C_{61}$-butyric acid methyl ester, a fullerene derivative, as a prototypical BHJ-OPV composition were drop-cast from 5 mg/mL (10 mg/mL for the polymer:fullerene blend) $CHCl_3$ solutions onto glass substrates that had been treated with a thin layer of PEDOT:PSS to allow proper solvent wetting and film formation. P3HT (a well-established crystalline organic semiconducting polymer, McCullough, R. D., et al., J. Am. Chem. Soc. 1993, 115, 4910) showed a diffraction peak at around 2θ=5°, while the other polymers and the blend showed no diffraction (FIG. 8). The lack of ordered aggregates in the polymer:fullerene blend may make these compounds suitable for use as organic photovoltaic (OPV) devices.

Excessive phase segregation is a known issue in bulk heterojunction photovoltaics, and M10A-containing polymers may help to prevent or slow the kinetics of polymer phase segregation while being able to interact with domains of crystalline curved PCBM molecular surfaces. Thin films were prepared in the same manner for UV-vis analysis, but were spin-coated onto glass-PEDOT:PSS substrates to yield films suitable for absorption analysis. The polymer films showed very slightly broadened UV-vis absorption traces relative to their solution spectra, indicating similar amounts of intermolecular interactions in the solid state and in solution. A notable amount of scattering was observed in many of the thin film spectra, so it is possible that unordered aggregates are present in the annealed solid state. Without wishing to be bound to any one particular theory, it is thought that the curved and racemic nature of the annulene unit in these polymers effectively suppresses π-π interactions or other specific types of polymer aggregation.

Thin Film Field-Effect Transistors.

Tail Out and No Tail PTMT-DPP were tested as p-type semiconducting materials using bottom-gate, top-contact organic field-effect transistors (OFETs). Note that no transistor performance was seen from Tail In PTMT-DPP.

The devices were prepared and tested under ambient atmospheric conditions using heavily n-doped Si wafers with 100-nm thermally grown native oxide. As shown in FIG. 9, the No Tail and Tail Out PTMT-DPP both performed as p-type semiconductors, but did not show n-type behavior despite the presence of the commonly ambipolar diketopyrrolopyrrole-co-thiophene motif. No Tail PTMT-DPP had a hole mobility of $1.44\times10^{-4}$ ($\pm0.17\times10^{-4}$) $cm^2/(V\ s)$ and a threshold voltage of −24 V. Tail Out PTMT-DPP had a hole mobility of $1.21\times10^{-4}$ ($\pm0.09\times10^{-4}$) $cm^2/(V\ s)$ and a threshold voltage of −29 V. These mobility values are lower than seen for semicrystalline DPP-containing polymers, but are comparable to disordered polymeric systems reported in the literature (ca. $10^{-3}$ to $10^{-4}$ $cm^2/(V\ s)$). Sonar, P., et al., Adv. Mater. 2010, 22, 5409; Li, Y., et al., J. Mater. Chem. 2011, 21, 10829; Chua, L.-L., et al., Nature 2005, 434, 194.

Four polymeric and two small molecule systems based on 1,6-methano[10]annulene were synthesized, with each system consisting of three different solubilizing side-chain arrangements: Tail In, Tail Out, and No Tail regioisomers. The polymer and oligomer families were designed to probe the reduction of torsional strain granted to nearby solubilizing alkyl chains by the curved geometry of the annulene, the extent of which was characterized by UV-vis and photoluminescence spectroscopy, as well as electrochemistry.

It was determined that 1,6-methano[10]annulene when incorporated into certain polymeric or oligomeric materials does grant a degree of steric relief that results in a longer effective conjugation length. The degree to which the conjugation is extended depends on the particular aromatic rings in the polymer and the placement of any solubilizing alkyl chains. For the PTMT, PTMT-B, and BTMTB series, 1,6-methano[10]annulene was found to grant a certain amount of steric relief when the hexyl chain was directed toward the annulene instead of toward another aromatic group. For the PTMT-T, PTMT-DPP, and TTMTT systems, the opposite effect was found due to the relatively small steric demands of the 2,5-thienyl group (2-thienyl in TTMTT series). The low-energy regions of the PTMT-DPP absorption spectra were dominated by the strongly absorbing DPP chromophores and their associated charge transfer bands. Cyclic voltammetry revealed that the polymers and small molecules maintain relatively similar HOMO energy levels. In addition to these electronic subtleties arising from torsional considerations, the polymers as thin films, including a PTMTB:PCBM blend, were all found to be disordered and possibly amorphous by XRD after drop-casting and annealing.

P-type field-effect transistors were prepared with No Tail and Tail Out PTMT-DPP and showed comparable mobilities and threshold values to other disordered polymeric systems operating under ambient conditions. The spectroscopic and device data reveal that conjugated polymers containing 1,6-methano[10]annulene may be useful in applications requiring highly disordered conjugated polymers Example 2

Materials and Methods

Synthesis.

Thiophene-appended annulene monomers were prepared through Stille couplings between the appropriate stannylated thienyl reagents and 2,7-dibromo-1,6-methano[10]annulene according to prior reports. These subunits were then brominated (NBS) or stannylated (lithiation and quenching with tributylstannyl chloride) at the substituted thiophene α-positions in order to be used in the synthesis of extended molecular models or polymers. Synthetic details are provided herein below.

NMR Spectroscopy.

All $^1$H and $^{13}$C NMR spectra were recorded in CDCl$_3$ or o-dichlorobenzene (o-DCB) (Cambride Isotope Laboratories) on a Bruker Avance 400 MHz instrument, and data were collected with either Bruker Topspin V.1.3 or 2.1, unless otherwise noted. Data were processed with either Topspin V.2.1 or SpinWorks V.3.1.7.0 (2010, University of Manitoba). All $^1$H spectra were calibrated against either residual protiochloroform (7.26 ppm) or TMS (0.00 ppm) in the deuterated solvent. $^{13}$C spectra were calibrated against the CDCl$_3$ triplet (77 ppm).

Gel Permeation Chromatography.

Polymer molecular weight analysis was carried out by gel permeation chromatography (GPC) on a Waters 1515 Isocratic HPLC equipped with two 5-mm Waters Styragel HR4 and HR3 columns (300 mm×7.8 mm), connected in series with increasing pore size, and a Waters 2489 UV-vis detector. Polymers are dissolved in HPLC grade tetrahydrofuran (0.5 mg/mL to 1 mg/mL) and filtered through a 0.2-mm PVDF filter. GPC was performed with submicrometer filtered HPLC grade THF (Fisher) eluent at 1 mL/min. The apparent molecular weight and polydispersity (PDI) were determined from a calibration curve based on linear polystyrene standards.

UV-Vis and Photoluminescence.

UV-vis spectra were taken on a Varian Cary 50 Bio UV-vis spectrometer in CHCl$_3$ (spectroscopic grade, Sigma-Aldrich) at ambient temperature using quartz cuvettes, unless otherwise noted. Solutions were spectroscopically dilute (ca. 10$^{-6}$ M) and had optical densities under 0.2. The data were collected and analyzed using Cary WinUV V.3.00(182) software. All fluorescence spectra were taken on a Photon Technology International fluorimeter fitted with a PTI 814 PMT for detection and PTI excitation and emission monochrom-eters. Spectra were recorded in CHCl$_3$ (spectroscopic grade, Sigma-Aldrich) at ambient temperature, using quartz cuvettes, unless otherwise noted. Excitation occurred at the lowest energy absorption maximum. PTI FeliX32 V.1.2 (Build 56) was used for data processing. Thin films were prepared by cleaning glass slides (Fisher) by sonication for 5 min each in Alconox solution, acetone, and isopropanol. Residual solvent was removed by blowing dry with nitrogen. The cleaned slides were treated with PEDOT:PSS (Sigma-Aldrich, high conductivity grade) and spun at 2000 rpm for 90 s, then annealed at 90° C. for 1 h, and allowed to cool to ambient temperature. Polymer solutions (1 mg/mL in o-dichlorobenzene) were spun onto the treated slides at 1200 rpm for 90 s and then annealed again at 90° C. for 15 min. A slide with only PEDOT:PSS was used as a 100% transmittance background sample. The samples were then placed in the beam path, and their absorption spectra were recorded.

Electrochemistry. All electrochemistry was performed on an Autolab potentiostat with a 2-mm Pt button working electrode, Pt wire counter electrode, and Ag/AgCl reference electrode, in either MeCN or DCM (spectroscopic grade, Sigma-Aldrich) with 0.1 M tetrabutylammonium hexafluorophosphate (TBAP) as the electrolyte. A ferrocene/ferrocenium external standard was used for all measurements. TBAP and ferrocene were obtained from Sigma-Aldrich, and the TBAP was recrystallized from anhydrous ethanol prior to use. Electrolyte solutions were stored over 4 Å molecular sieves. Data were collected and processed using GPES software.

X-Ray Diffraction.

5 mg/mL solutions in CHCl$_3$ of each polymer (5 mg/mL each of Tail In PTMTB and PC61BM for the bulk heterojunction film) were prepared by heating and sonicating the mixture extensively. Glass slides (Fisher premium) were sonicated for 5 min each in DI H$_2$O, isopropanol, and acetone (all spectroscopic grade), before drying with dry nitrogen. A thin layer of PEDOT:PSS (Sigma-Aldrich, high conductivity grade) was spin-coated onto the clean substrates at 2500 rpm for 90 s and annealed for 1 h at 90° C. before being allowed to cool. The films were drop-cast on and annealed at 90° C. for 3 min. A Cu Kα source and PIXcel-3D detector were used to effect a 2θ scan with a set omega at 0.3°, a scan range of 1.996°-25.000°, step size of 0.013 130 3°, and a scan speed of 0.016726 deg/s.

Transistor Fabrication.

Bottom gate-top contact transistors were fabricated on highly doped n-type Si wafers (SI-Tech, Process Solutions) with a thermally grown 100-nm oxide layer. All wafers were sonicated in warm acetone and IPA and dried in a stream of dry nitrogen. Active layers of 1,6-methano[10]annulene-containing polymers were spin-coated (Laurell Technologies Corporation) at 1500 rpm for 90 s and annealed at 90° C. for 5 min. Wafers were loaded overnight for thermal evaporation of 125-nm Au electrodes (Edwards Auto 306) through a shadow mask with W/L ratio of 32, where W=8 mm and L=250 μm. Si gates were scratched with a diamond scribe and contacted with Ga—In eutectic (Sigma-Aldrich). All electrical characterization was performed on an Agilent 4155C Semiconductor Parameter Analyzer using a medium integration time (16.7 ms), under ambient fluorescent lighting conditions, in air. Devices were probed with low-resistance probes from Micromanipulator, onto which small (approximately 100 μm) drops of Ga—In eutectic were placed for contacting source and drain electrodes.

Example 2

General Methods

All column chromatography solvents were distilled technical grade. All palladium and nickel catalysts were obtained from Strem Chemicals and used as received. 2,2'-bipyridyl, 2-bromothiophene, 2-tributylstannylthiophene, n-butyllithium, toluene, and DMF were obtained from Sigma Aldrich and used as received, except for toluene and DMF, which were dried over 4 Å molecular sieves and sparged for 0.5-1 h with dry $N_2$. N-bromosuccinimide (NBS) was obtained from Sigma Aldrich and was recrystallized from water before use. 1,5-cyclooctadiene (COD) was obtained from JT Baker Chemicals and distilled prior to use. 1,6-methano[10]annulene, Vogel, E.; Roth, H. D. *Angew. Chem.* 1964, 76, 145; 2,7-dibromo-1,6-methano[10]annulene, Vogel, E.; Klug, W.; Breuer, A. *Org. Synth.* 1974, 54, 11; No Tail TMT, Peart, P. A.; Repka, L. M.; Tovar, J. D. *Eur. J. Org. Chem.* 2008, 22, 3875; 4,7-dibromo-2,1,3-benzothiadiazole, Pilgram, K. J.; *J. Het. Chem.* 1970, 7, 629; and 3,6-bis(2-bromo-5-thienyl)-2,5-di(2-ethylhexyl)pyrrole[3,4-c]-pyrrole-1,4-(2H,5H)-dione, Woo, C. H.; Beaujuge, P. M.; Holcombe, T. W.; Lee, O. P.; Fréchet, J. M. J. *J. Am. Chem. Soc.* 2010, 132, 15547; were prepared according to literature procedures.

Example 3

General Procedure for TMT Synthesis 2,7-dibromo-1,6-methano[10]annulene (1.0 equiv), 2-tributylstannyl)thiophene (2.2 equiv), and $(PPh_3)_2PdCl_2$ (0.05 equiv) were added to a flame dried Schlenk flask charged with a magnetic stir bar and evacuated/refilled with dry $N_2$ three times. 20 mL dry, degassed toluene was added via syringe and the solution was stirred and heated to 105° C. for 15 h. At this point, the solution was allowed to cool while stirring and then poured into a rapidly stirring mixture of diethyl ether and 1M KF (aq) (50 mL of each). This suspension was stirred for 5-10 min and vacuum filtered. 50 mL of the KF solution was added and stirred for 5 more min before vacuum filtration. The organic layer was separated and dried with $MgSO_4$, the solvent was removed by rotary evaporation, and the crude solid dried under high vacuum. The crude material was purified by column chromatography on $SiO_2$ with hexanes as the eluent.

2,7-bis(4-hexyl-2-thienyl)-1,6-methano[10]annulene (Tail Out TMT)

Prepared according to general TMT synthesis procedure using 2,7-dibromo-1,6-methano[10]annulene (0.5003 g, 1.6667 mmol), 5-tributylstannyl-3-hexylthiophene (1.9121 g, 4.1809 mmol), and Pd(PPh3)2Cl2 (49.6 mg, 0.0706 mmol). The product was isolated as a fluorescent yellow oil (0.6318 g, 1.331 mmol, 80%). 1H NMR (400 MHz, $CDCl_3$) δ: 7.86 (d, J=9 Hz, 2H), 7.40 (d, J=9 Hz, 2H), 7.32 (s, 2H), 7.08 (t, J=9 Hz, 2H), 6.94, (s, 2H), 2.65 (t, 4H, J=6.0 Hz), 1.68 (m, 4H), 1.34 (m, 12H), 0.90 (t, 6H, J=6.0 Hz), −0.08 (s, 2H); 13C NMR (100 MHz, $CDCl_3$) δ: 144.2, 142.8, 135.4, 130.0, 129.0, 128.0, 121.4, 117.9, 36.0, 31.8, 30.7, 30.6, 29.1, 22.7, 14.2. UV-Vis ($CHCl_3$): $\lambda_{max}$ 289 nm (ε=30100 $M^{-1}$ $cm^{-1}$), 383 nm (ε=20900 $M^{-1}$ $cm^{-1}$). HRMS (EI) Calcd for C31H38S2: 474.2417 [M+•], Found m/z=474.2415.

2,7-bis(3-hexyl-2-thienyl)-1,6-methano[10]annulene (Tail in TMT)

Prepared according to general TMT synthesis procedure using 2,7-dibromo-1,6-methano[10]annulene (0.5007 g, 1.6667 mmol), 2-tributylstannyl-3-hexylthiophene (1.6851 g, 3.6846 mmol), and Pd(PPh3)2Cl2 (49.8 mg, 0.0708 mmol). The product was isolated as a fluorescent yellow oil (0.5212 g, 1.0978 mmol, 66%). 1H NMR (400 MHz, $CDCl_3$) δ: 7.29 (d, J=10 Hz, 2H), 7.17 (d, J=5 Hz, 2H), 7.13 (d, J=10 Hz, 2H), 6.96 (m, J=5, 10 Hz, 4H), 2.90 (m, 2H) 2.74 (m, 2H), 1.40 (m, 4H), 1.07 (m, 12H), 0.71 (t, J=6 Hz, 6H), −0.15 (s, 2H); 13C NMR (100 MHz, $CDCl_3$): δ 140.6, 136.2, 133.8, 129.4, 128.8, 126.5, 124.7, 117.0, 34.9, 31.2, 30.2, 28.7, 22.2, 13.8. UV-Vis ($CHCl_3$): $\lambda_{max}$ 285 nm (ε=35800 $M^{-1}$ $cm^{-1}$), 365 nm (ε=18000 $M^{-1}$ $cm^{-1}$). HRMS (EI) Calcd for C31H38S2: 474.2415 [M+•] Found m/z=474.2402.

Example 4

General Procedure for Bromination of TMTs 2,7-bis(3-hexyl-2-thienyl)-1,6-methano[10]annulene (0.80 mmol, 1.0 equiv) and NBS (1.69 mmol, 2.1 equiv) were added to a roundbottom flask charged with a stir bar. The flask was completely wrapped in aluminum foil to exclude light. Dichloromethane (5 mL) was added and flask vented by insertion of a needle through a septum in the neck of the flask. The reaction was stirred at ambient temperature for 2-3 d. The mixture was diluted with 20 mL hexanes and the organic layer washed with water (2×15 mL) and brine (1×15 mL) before the organic layer was dried with MgSO4. The solvent was removed by rotary evaporation and the crude product placed under high vacuum. The crude material was purified by column chromatography on SiO2, with hexanes as the eluent. Note: the dibromo-No Tail TMT was purified by recrystallization from boiling ethanol.

5',5"-dibromo-2,7-bis(4-hexyl-2-thienyl)-1,6-methano[10]annulene (Dibromo-Tail Out TMT)

Prepared according to the general TMT bromination procedure using 2,7-bis(4-hexyl-2-thienyl)-1,6-methano[10]annulene (0.2506 g, 0.2633 mmol), N-bromosuccinimide (0.0961 g, 0.5397 mmol), dichloromethane (7 mL). Column chromatography (silica/hexane) gave pure compound (0.2399 g, 0.3793 mmol, 72%). 1H NMR (400 MHz, $CDCl_3$) δ: 7.82 (d, J=8.8 Hz, 2H), 7.31 (d, J=9.0 Hz, 2H), 7.14 (s, 2H), 7.07 (t, J=9.0 Hz, 2H), 2.60 (t, J=6.0 Hz, 4H), 1.64 (m, 4H), 1.34 (m, 12H), 0.90 (m, 6H), −0.013 (s, 2H). 13C NMR (100 MHz, $CDCl_3$) δ: 142.9, 142.2, 134.3, 129.9, 128.2, 127.9, 126.9, 117.6, 109.8, 35.6, 31.5, 29.6, 29.5, 28.8, 22.4, 13.9. HR-MS (EI) Calcd for C31H36S2Br2: 634.0605 [M+•] Found m/z=634.0605

5',5"-dibromo-2,7-bis(3-hexyl-2-thienyl)-1,6-methano[10]annulene (Dibromo-Tail In TMT)

Prepared according to the general TMT bromination procedure using 2,7-bis(3-hexyl-2-thienyl)-1,6-methano[10]annulene (0.4747 g, 0.9999 mmol), N-bromosuccinimide (0.3663 g, 2.0581 mmol), dichloromethane (10 mL). Column chromatography (silica/hexane) gave pure compound (0.4553 g, 0.7198 mmol, 72%). 1H NMR (400 MHz, $CDCl_3$) δ: 7.39 (d, J=8.7 Hz, 2H), 7.16 (d, J=9.5 Hz, 2H), 7.03 (t, J=9.1 Hz, 2H), 6.99 (s, 2H), 2.85-2.65 (m, 4H), 1.51 (m, 4H), 1.14 (m, 12H), 0.79 (t, J=6.0 Hz, 6H), −0.013 (s, 2H). 13C NMR (100 MHz, $CDCl_3$) δ: 141.6, 138.2, 133.0, 132.0, 130.0, 129.3, 127.0, 117.5, 111.8, 34.9, 31.6, 30.4, 29.3, 28.9, 22.7, 14.0. HR-MS (EI) Calcd for C31H36S2Br2 [M+•]: 632.06015 Found m/z=632.06047.

5',5"-dibromo-2,7-bis(2-thienyl)-1,6-methano[10] annulene (Dibromo-No Tail TMT)

Prepared according to the general TMT bromination procedure using 2,7-bis(2-thienyl)-1,6-methano[10]annulene (0.2504 g, 0.8160 mmol), N-bromosuccinimide (0.3061 g, 1.7199 mmol), dichloromethane (4 mL). Recrystallization from MeOH gave a pure solid product (0.1546 g, 0.3331 mmol, 41%). 1H NMR (400 MHz, CDCl$_3$) δ: 7.81 (d, J=8.6 Hz, 2H), 7.31 (d, J=9.6 Hz, 2H), 7.18 (d, J=3.9 Hz, 2H), 7.10-7.07 (m, 4H), −0.05 (s, 2H). 13C NMR (100 MHz, CDCl$_3$) δ: 144.4, 133.9, 130.6, 130.0, 128.1, 127.5, 127.1, 117.5, 113.0, 35.5.

Example 5

General Procedure for bis(tributylstannyl)-TMT Synthesis 2,7-bis(2-thienyl)-1,6-methano[10]annulene (0.33 mmol, 1.0 equiv) was added to a flame dried Schlenk flask charged with a stir bar and evacuated/refilled with dry N$_2$ three times. Distilled THF (10 mL) was added and the solution stirred while cooling to −78° C. in a dry ice/acetone bath for 20 min. N-Butyl-lithium solution (1.6 M, 0.50 mL, 2.2 equiv) was added dropwise, and the solution stirred for an hour while maintaining the temperature at −78° C. Tributyltin chloride (0.2 mL, 2.2 equiv) was added via syringe and the solution stirred at −78° C. for one hour before removing the cooling bath and allowing the mixture to warm to room temperature overnight. The reaction was quenched with DI H$_2$O (10 mL) and extracted with dichloromethane (25 mL). The organic layer was washed with water (3×15 mL) and brine (1×15 mL) before drying with MgSO$_4$. The solvent was removed by rotary evaporation, and the crude material placed under high vacuum. The crude product was carried on as is, using NMR integrations as estimates of purity for accurate additions in later reactions.

5',5"-bis(tributylstannyl)-2,7-bis(4-hexyl-2-thienyl)-1,6-methano[10]annulene (Bis-stannyl Tail Out TMT)

2,7-bis(4-hexyl-2-thienyl)-1,6-methano[10]annulene (0.2492 g, 0.5249 mmol), n-butyllithium (0.85 mL, 1.62 M), tributyltin chloride (0.33 mL, 1.1058 mmol), THF (15 mL). The product was isolated as a crude yellow oil. The crude product showed a very clean aromatic $^1$H NMR region, but contained excess tributyltin chloride which proved very difficult to remove. $^1$H NMR (400 MHz, CDCl$_3$) δ: 7.87 (d, J=8.8 Hz, 2H), 7.48 (s, 2H), 7.42 (d, J=9.7 Hz, 2H), 7.08 (t, J=9.3 Hz, 2H), 2.61 (m, 4H), 1.75-1.50 (m, 16H), 1.35 (m, 24H), 1.14 (m, 8H), 0.91 (t, J=6.0 Hz, 24H), −0.07 (s, 2H).

5',5"-bis(tributylstannyl)-2,7-bis(3-hexyl-2-thienyl)-1,6-methano[10]annulene (Bis-stannyl Tail In TMT)

2,7-bis(3-hexyl-2-thienyl)-1,6-methano[10]annulene (0.2642 g, 0.5266 mmol), n-butyllithium (0.85 mL, 1.62 M), tributyltin chloride (0.33 mL, 1.1058 mmol), THF (15 mL). The product was isolated as a crude yellow oil. The crude product showed a very clean aromatic 1H NMR region, but contained excess tributyltin chloride which proved very difficult to remove. 1H NMR (400 MHz, CDCl$_3$) δ: 7.87 (d, J=8.8 Hz, 2H), 7.50 (s, 2H), 7.42 (d, J=9.7 Hz, 2H), 7.08 (t, J=9.3 Hz, 2H), 2.61 (m, 4H), 1.75-1.50 (m, 16H), 1.35 (m, 24H), 1.14 (m, 8H), 0.91 (t, J=6.0 Hz, 24H), −0.07 (s, 2H).

5',5"-bis(tributylstannyl)-2,7-bis(2-thienyl)-1,6-methano[10]annulene (Bis-stannyl No Tail TMT)

2,7-bis(2-thienyl)-1,6-methano[10]annulene (0.1002 g, 0.3263 mmol), n-butyllithium (0.52 mL, 1.62 M), tributyltin chloride (0.19 mL, 0.6820 mmol), THF (15 mL). The product was isolated as a crude yellow oil. The crude product showed a very clean aromatic 1H NMR region, but contained excess tributyltin chloride which proved very difficult to remove. 1H NMR (400 MHz, CDCl$_3$) δ: 7.86 (d, J=8.8 Hz, 2H), 7.50 (d, J=8.0 Hz, 2H), 7.43 (d, J=9.7 Hz, 2H), 7.08 (t, J=9.3 Hz, 2H), 1.62 (m, 12H), 1.36 (m, 12H), 1.14 (m, 12H), 0.91 (t, J=6.0 Hz, 18H), −0.05 (s, 2H).

Example 6

General Procedure for Stille Cross-Coupling Polymerization

Aryl dibromide (0.5 mmol, 1.0 equiv.), aryl distannane (0.5 mmol, 1.0 equiv.), Pd(PPh3)2Cl2 (0.025 mmol, 0.05 equiv), CsF (2.2 mmol, 4.4 equiv), and CuI (0.1 mmol, 0.2 equiv) are added to a flame dried Schlenk flask and evacuated/refilled with N2 three times. Toluene that has been degassed with dry N2 over 4 Å sieves for 30 min is added to dibromide and distannane and magnetically stirred to dissolve. The solution is heated to 105° C. and stirred for 1-5 d until the reaction mixture is allowed to cool and concentrated by rotary evaporation. The resulting crude solid is dissolved in CHCl$_3$ and precipitated into rapidly stirring room temperature MeOH. The precipitate is then washed with excess MeOH to remove monomer and catalyst.

Tail Out PTMT-B (Prepared According to General Stille Polymerization Procedure).

5',5"-bis(tributylstannyl)-2,7-bis(4-hexyl-2-thienyl)-1,6-methano[10]annulene (0.3502, 0.3324 mmol), 4,7-dibromo-2,1,3-benzothiadiazole (0.0769 g, 0.2618 mmol), Pd(PPh$_3$)$_4$ (0.0074 g, 0.0105 mmol). $^1$H NMR (400 MHz, CDCl$_3$) δ: 8.02 (m, br), 7.75 (s, br), 7.55 (m, br), 7.18 (m, br), 2.78 (m, br), 1.74 (m, br), 1.57 (s, br), 1.30 (m, br), 0.84 (m, br), 0.07 (s). GPC: Mw=7743 g/mol, Mn=3019 g/mol, PDI=2.57, DPw: 12.8. UV-Vis (CHCl$_3$): λ$_{max}$ 480 nm, onset 600 nm.

Tail In PTMT-B (Prepared According to General Stille Polymerization Procedure).

5',5"-bis(tributylstannyl)-2,7-bis(3-hexyl-2-thienyl)-1,6-methano[10]annulene (0.3508 g, 0.3325 mmol), 4,7-dibromo-2,1,3-benzothiadiazole (0.0772 g, 0.2621 mmol), Pd(PPh$_3$)$_4$ (0.0073 g, 0.0105 mmol). 1H NMR (400 MHz, CDCl$_3$) δ: 8.12 (s, br), 7.89 (s, br), 7.54 (d, J=8.4 Hz), 7.36 (d, J=10.5 Hz), 7.14 (t, J=9.1 Hz), 7.06 (m, br), 3.07 (m, br), 2.90 (m, br), 1.79-1.51 (m, br), 1.38-1.16 (m, br), 0.82 (m, br), 0.03 (s). GPC: Mw=7822 g/mol, Mn=3820 g/mol, PDI=2.05, DPw: 12.9 UV-Vis (CHCl$_3$): λ$_{max}$ 523 nm, onset 630 nm.

No Tail PTMT-B (Prepared According to General Stille Polymerization Procedure).

5',5"-bis(tributylstannyl)-2,7-bis(2-thienyl)-1,6-methano[10]annulene (0.1101 g, 0.1242 mmol), 4,7-dibromo-2,1,3-benzothiadiazole (0.0320 g, 0.1089 mmol), Pd(PPh3)4 (0.0030 g, 0.0049 mmol). 1H NMR (400 MHz, o-DCB): 8.21 (m, br), 7.96 (m, br), 7.60 (m, br), 7.23 (m, br), 3.15 (s, br), 2.37 (s, br), 1.30 (m, br), 0.92 (s, br), 0.08 (s, br). GPC: Poor solubility prevents analysis using THF. UV-Vis (CHCl$_3$): λ$_{max}$ 520 nm, onset 610 nm.

(Tail Out PTMT-T) (Prepared According to General Stille Polymerization Procedure).

5',5"-dibromo-2,7-bis(4-hexyl-2-thienyl)-1,6-methano[10]annulene (100.0 mg, 0.1581 mmol), 2,5-bistributylstannylthiophene (104.7 mg, 0.1581 mmol), PdCl2(PPh3)2 (5.6 mg, 0.0079 mmol), 5 mL Toluene. Yielded 21.8 mg (59%) of an orange powder. 1H NMR (400 MHz, CDCl$_3$) δ: 7.93-7.87 (m, br), 7.44-7.33 (m, br), 7.15-7.10 (m, br), 6.97 (s, Ar), 2.87 (m, br), 2.66 (m, br), 1.80-1.57 (m, br), 1.35 (s, br), 0.91 (m, br), −0.04 (s, CH2). GPC: Mw=14987 g/mol, Mn=5691 g/mol, PDI=2.63, DPw: 27.0. UV-Vis (CHCl$_3$): $\lambda_{max}$ 435 nm, onset 575 nm.

Tail In PTMT-T (Prepared According to General Stille Polymerization Procedure).

5',5"-dibromo-2,7-bis(3-hexyl-2-thienyl)-1,6-methano[10]annulene (100.0 mg, 0.1581 mmol), 2,5-bistributylstannylthiophene (104.7 mg, 0.1581 mmol), PdCl$_2$(PPh$_3$)$_2$ (5.6 mg, 0.0079 mmol), 5 mL Toluene. Yielded 20.4 mg (58%) of an orange powder. 1H NMR (400 MHz, CDCl$_3$) δ: 7.47 (m, br), 7.35 (m, br), 7.15 (s), 7.07 (m), 2.91 (m, br), 2.75 (m, br), 2.00-1.71 (m), 1.65 (m, br), 1.42 (m), 1.18 (m, br), 0.95 (t, J=7.2 Hz), −0.05 (s). GPC: Mw=11141 g/mol, Mn=3587 g/mol, PDI=3.11, DPw: 20.0. UV-Vis (CHCl$_3$): $\lambda_{max}$ 422 nm, onset 540 nm.

No Tail PTMT-T (Prepared According to General Stille Polymerization Procedure).

5',5"-dibromo-2,7-bis(2-thienyl)-1,6-methano[10]annulene (100.0 mg, 0.1581 mmol), 2,5-bistributylstannylthiophene (104.7 mg, 0.1581 mmol), PdCl$_2$(PPh$_3$)$_2$ (5.6 mg, 0.0079 mmol), 5 mL Toluene. Yielded 14.0 mg of an orange powder. 1H NMR (400 MHz, o-DCB) δ: 7.90 (m, br), 7.85 (d, J=8.8 Hz), 7.48 (m, br), 7.44-7.42 (m, br), 7.36 (d, J=5.2 Hz), 7.15-7.10 (m, br), −0.02 (s). GPC: Poor solubility prevents analysis using THF. UV-Vis (CHCl$_3$): $\lambda_{max}$ 455 nm, onset 560 nm.

Tail Out PTMT-DPP (Prepared According to General Stille Polymerization Procedure).

5',5"-bis(tributylstannyl)-2,7-bis(4-hexyl-2-thienyl)-1,6-ethano[10]annulene (0.1542 g, 0.1465 mmol), 3,6-bis(2-bromo-5-thienyl)-2,5-di(2-ethylhexyl)pyrrole[3,4-c]-pyrrole-1,4-(2H,5H)-dione (50.0 mg, 0.0733 mmol), CsF (49.0 mg, 0.3223 mmol), CuI (2.8 mg, 0.014 mmol), (PPh$_3$)$_4$Pd (42.3 mg, 0.037 mmol), and toluene (7 mL). Yielded 85.3 mg of dark blue-green powder (39%). 1H NMR (400 MHz, CDCl$_3$) δ: 9.07 (m), 7.95-7.88 (m, br), 7.48-7.32 (m, br), 7.14 (q, J=9.7 Hz), 6.97 (s), 4.06 (m, br), 2.90 (m, br), 2.65 (m, br), 1.95 (s, br), 1.77 (m, br), 1.68 (m, br), 1.53 (s), 1.44-1.24 (m, br), 0.90 (m, br), 0.06 (s). GPC: Mw: 4742 g/mol Mn: 3003 g/mol PDI: 1.58 DPw: 4.8. UV-Vis (CHCl$_3$): $\lambda_{max}$ 636 nm, onset 810 nm.

Tail In PTMT-DPP (Prepared According to General Stille Polymerization Procedure).

5',5"-bis(tributylstannyl)-2,7-bis(3-hexyl-2-thienyl)-1,6-methano[10]annulene (0.1546 g, 0.1466 mmol), 3,6-bis(2-bromo-5-thienyl)-2,5-di(2-ethylhexyl)pyrrole[3,4-c]-pyrrole-1,4-(2H,5H)-dione (50.4 mg, 0.0733 mmol), CsF (48.7 mg, 0.3223 mmol), CuI (3.0 mg, 0.013 mmol), (PPh$_3$)$_4$Pd (4.2 mg, 0.0037 mmol), and toluene (5 mL). Yielded 79.2 mg of dark blue-green powder (36%). 1H NMR (400 MHz, CDCl$_3$) δ: 8.97 (m, br), 7.44 (m, br), 7.30 (m, br), 7.09 (m, br), 4.06 (m, br), 1.94 (s, br), 1.54 (s, br), 1.54-1.42 (m, br), 0.94-0.78 (m, br), 0.06 (s). GPC: Mw: 5517 g/mol Mn: 3203 g/mol PDI: 1.72 DPw: 5.5. UV-Vis (CHCl$_3$): $\lambda_{max}$ 637 nm, onset 810 nm.

No Tail PTMT-DPP (Prepared According to General Stille Polymerization Procedure).

5',5"-bis(tributylstannyl)-2,7-bis(2-thienyl)-1,6-methano[10]annulene (64.9 mg, 0.0733 mmol), 3,6-bis(2-bromo-5-thienyl)-2,5-di(2-ethylhexyl)pyrrole[3,4-c]-pyrrole-1,4-(2H, 5H)-dione (50.0 mg, 0.0733 mmol), (PPh3)2PdCl2 (2.6 mg, 0.0037 mmol), and toluene (5 mL). Yielded 65.0 mg of dark blue-green powder (30%). 1H NMR (400 MHz, o-DCB) δ: 8.97 (m, br), 7.92 (br), 7.49-7.43 (m, br), 7.38 (m, br), 7.16 (m, br), 4.05 (s, br), 1.94 (s, br), 1.46-1.19 (m, br), 0.89 (m, br), 0.07 (s). GPC: Poor solubility prevents analysis using THF. UV-Vis (CHCl$_3$): $\lambda_{max}$ 644 nm, onset 803 nm.

General Procedure for Yamamoto Polymerization:

Prepared according to literature procedures. Yamamoto, T.; et al. *Macromolecules* 1992, 25, 1214.

Ni(COD)$_2$ (0.1000 mmol, 1.2 equiv), 2,2'-bipyridine (0.1000 mmol, 1.2 equiv), and COD (0.8333 mmol, 1.0 equiv) are added to a flame dried Schlenk flask charged with a stir bar. The flask is evacuated and refilled 3 times with N2, after which a portion of dry, degassed DMF (1-3 mL) is added. The mixture is stirred for 30 min at room temperature, during which the mixture goes from yellow to deep purple. While stirring, aryl dibromide (0.08 mmol, 1.0 equiv) is added to a separate Schlenk flask, evacuated/refilled three times and dissolved in dry, degassed DMF (1-2 mL). This solution is added via syringe to the Ni(bipy)COD complex in the first flask, and heated to 60° C. for 48-96 h. Upon completion the reaction mixture is precipitated from rapidly stirring MeOH and the polymer collected via vacuum filtration.

Tail Out PTMT (Prepared According to General Yamamoto Polymerization Procedure).

5',5"-dibromo-2,7-bis(4-hexyl-2-thienyl)-1,6-methano[10]annulene (108.4 mg, 0.1714 mmol), Ni(COD)2 (56.6 mg, 0.2056 mmol), COD (18.0 mg, 0.1714), 2,2'-bipyridyl (32.1 mg, 0.2056 mmol), 5 mL DMF. Yielded 51.0 mg (63.0%) of an orange powder. 1H NMR (400 MHz, CDCl$_3$) δ: 7.96 (br), 7.84 (br), 7.47 (m, br), 7.40 (s, br), 7.15 (m, br), 2.66 (s, br), 1.67 (s, br), 1.30 (s, br), 0.88 (s, br), −0.05 (br). GPC: Mw=4920 g/mol, Mn=2402 g/mol, PDI=2.05, DPw: 10.4. UV-Vis (CHCl$_3$): $\lambda_{max}$ 418 nm, onset 513 nm.

Tail In PTMT (Prepared According to General Yamamoto Polymerization Procedure).

5',5"-dibromo-2,7-bis(3-hexyl-2-thienyl)-1,6-methano[10]annulene (50.0 mg, 0.0790 mmol), Ni(COD)$_2$ (26.1 mg, 0.0949 mmol), COD (8.5 mg, 0.0790), 2,2'-bipyridyl (14.8 mg, 0.0949 mmol), 2 mL DMF. Yielded 21.8 mg (58.4%) of an orange powder. 1H NMR (400 MHz, CDCl$_3$) δ: 7.49 (m, br), 7.15 (m, br), 2.95-2.75 (m, br), 1.64 (m, br), 1.21 (m, br), 0.82 (m, br), −0.01 (s, br). GPC: Mw=6169 g/mol, Mn=3828 g/mol, PDI=1.61, DPw: 13.0 UV-Vis (CHCl$_3$): $\lambda_{max}$ 430 nm, onset 520 nm.

No Tail PTMT (Prepared According to General Yamamoto Polymerization Procedure).

5',5"-dibromo-2,7-bis(2-thienyl)-1,6-methano[10]annulene (100.0 mg, 0.2154 mmol), Ni(COD)$_2$ (71.1 mg, 0.2583 mmol), COD (23.3 mg, 0.2154), 2,2'-bipyridyl (40.4 mg, 0.2583 mmol), 5 mL DMF. Yielded 9.5 mg (14.4%) of a red powder. 1H NMR (400 MHz, o-DCB) δ: 7.92 (m, br), 7.85 (d, J=8.5 Hz), 7.49-7.35 (m, br), 7.16-7.07 (m, br), 0.05, (s). GPC: Poor solubility prevented analysis using THF. UV-Vis (CHCl$_3$): $\lambda_{max}$ 468 nm, onset 540 nm.

Example 7

General Procedure for Stille Cross-Coupling of Small Molecule Systems

Aryl dibromide (0.1000 mmol, 1.0 equiv), bisstannylarene (0.2250 mmol, 2.25 equiv), and PdCl$_2$(PPh$_3$)$_2$ (0.0050 mmol, 0.05 equiv) or Pd(PPh$_3$)$_4$ (0.0050 mmol, 0.05 equiv), were added to a flame dried, N$_2$ filled Schlenk flask with a stir bar.

The flask was evacuated/refilled 3×, at which point dry, degassed toluene (DMF) is added. The solution is heated to 105° C. (80° C.) while stirring for 48-96 h, while monitoring progress with TLC. Upon completion the reaction mixture is diluted with ethyl ether and stirred with ~50 mL 1M KF for 10 min. The resulting precipitate is vacuum filtered and the organic layer is separated and stirred with another 50 mL KF solution. Again the solution is filtered, the organic layer separated, washed with saturated aq. NH$_4$Cl, and dried over MgSO$_4$. The solvent is removed via rotary evaporation, and the crude material purified by column chromatography (SiO$_2$).

5',5"-bis(2-thienyl)-2,7-bis(4-hexyl-2-thienyl)-1,6-methano[10]annulene (Tail Out TTMTT) (Prepared According to General Stille TTMTT Procedure)

5',5"-dibromo-2,7-bis(4-hexyl-2-thienyl)-1,6-methano[10]annulene (50.0 mg, 0.0790 mmol), 2-tributylstannylthiophene (66.5 mg, 0.1778 mmol), PdCl$_2$(PPh$_3$)$_2$ (5.4 mg, 0.0079 mmol), 3 mL toluene. After 72 hours reaction was quenched, and chromatographed using 95:5 hexane:ethyl acetate mixture as eluent. Yielded 23.3 mg (46.1%) orange powder. 1H NMR (400 MHz, CDCl$_3$) δ: 7.91 (d, J=8.7 Hz, 2H), 7.42 (d, J=9.6 Hz, 2H), 7.31 (m, 2H), 7.17 (s, 2H), 7.11 (m, 4H), 2.81 (m, 4H), 1.71 (m, 4H), 1.43 (m, 4H), 1.33 (m, 8H), 0.90 (m, 6H), −0.04 (s, 2H). 13C NMR (100 MHz, CDCl$_3$): δ 140.9, 140.5, 136.3, 132.1, 130.2, 128.1, 127.5, 127.2, 118.1, 36.0, 31.8, 30.7, 29.6, 29.4, 22.7, 14.2. HRMS (EI) Calcd for C39H42S4: 638.21694 [M+•] Found m/z=638.21691. UV-Vis (CHCl$_3$): λ$_{max}$ 414 nm (ε=43500 M$^{-1}$ cm$^{-1}$).

5',5"-bis(2-thienyl)-2,7-bis(3-hexyl-2-thienyl)-1,6-methano[10]annulene (Tail In TTMTT) (Prepared According to General Stille TTMTT Procedure)

5',5"-bis(tributylstannyl)-2,7-bis(3-hexyl-2-thienyl)-1,6-methano[10]annulene (50.5 mg, 0.0475 mmol), 2-bromothiophene (17.1 mg, 0.1045 mmol), Pd(PPh$_3$)$_4$ (2.7 mg, 0.0024 mmol), 3 mL DMF. After 48 hours reaction was quenched, and chromatographed using hexane as eluent. Yielded 6.4 mg (21.1%) orange powder. 1H NMR (400 MHz, CDCl$_3$) δ: 7.46 (d, J=8.8 Hz, 2H), 7.20 (d, J=5.4 Hz, 2H), 7.17 (d, J=3.0 Hz, 2H), 7.14 (s, 2H), 7.08 (t, J=9.4 Hz, 4H), 7.02 (m, 2H) 2.92 (m, 4H), 2.76 (m, 4H), 1.56 (m, 4H), 1.19 (m, 8H), 0.81 (m, 6H), −0.05 (s, 2H). 13C NMR (100 MHz, CDCl$_3$) δ: 141.7, 140.9, 140.4, 137.6, 136.7, 135.5, 133.7, 130.2, 129.1, 127.8, 126.9, 125.8, 124.2, 123.3, 117.5, 35.5, 31.7, 30.4, 29.4, 28.9, 22.5, 14.0. HRMS (EI) Calcd for C39H42S4: 638.21694 [M+•] Found m/z=638.21518. UV-Vis (CHCl$_3$): λ$_{max}$ 389 nm (ε=38000 M$^{-1}$ cm$^{-1}$).

5',5"-bis(2-thienyl)-2,7-bis(2-thienyl)-1,6-methano[10]annulene (No Tail TTMTT) (Prepared According to General Stille Small Molecule Procedure)

5',5"-bis(tributylstannyl)-2,7-bis(2-thienyl)-1,6-methano[10]annulene (50.5 mg, 0.1077 mmol), 2-tributylstannylthiophene (90.4 mg, 0.2423 mmol), PdCl2(PPh3)2 (3.8 mg, 0.0054 mmol), 3 mL Toluene. After 96 hours reaction was quenched, and chromatographed using hexane as eluent. Yielded 7.8 mg (15.4%) orange powder. 1H NMR (400 MHz, CDCl$_3$) δ: 7.82 (d, J=8.6 Hz, 2H), 7.35 (d, J=9.5 Hz, 2H), 7.17 (m, 2H), 7.17 (s, 2H), 7.14 (m, 4H), 7.04 (t, J=9.2 Hz, 4H), 6.96 (m, 2H) −0.08 (s, 2H). 13C NMR (100 MHz, CDCl$_3$) δ: 142.9, 141.9, 138.3, 137.3, 134.5, 130.0, 127.9, 126.9, 124.4, 123.5, 117.8, 35.7. HRMS (EI) Calcd for C27H18S4: 470.02914 [M+•] Found m/z=470.02866. UV-Vis (CHCl$_3$): λ$_{max}$ 417 nm (ε=25000 M$^{-1}$ cm$^{-1}$).

5',5"-bis(4-2,1,3-benzothiadiazole)-2,7-bis(4-hexyl-2-thienyl)-1,6-methano[10]annulene (Tail Out BTMTB) (Prepared According to General Stille Small Molecule Procedure)

5',5"-bis(tributylstannyl)-2,7-bis(4-hexyl-2-thienyl)-1,6-methano[10]annulene (100.0 mg, 0.956 mmol), 4-bromo-2,1,3-benzothiadiazole (42.9 mg, 0.1995 mmol), (PPh3)4PdCl2 (3.3 mg, 0.0047 mmol), and toluene (5 mL). Yielded 7.5 mg of a red powder (11%). 1H NMR (400 MHz, CDCl$_3$) δ: 8.01 (t, J=10.0 Hz, 2H), 7.68 (m, 2H), 7.52 (d, J=8.4 Hz, 2H), 7.15 (t, J=9.0 Hz, 1H), 2.70 (m, 4H), 1.69 (m, 4H), 1.25 (m, 12H), 0.83 (m, 6H), 0.05 (s, 2H). 13C NMR (100 MHz, CDCl$_3$) δ: 131.7, 130.7, 129.7, 128.6, 127.9, 127.0, 125.55, 120.7, 119.8, 31.5, 30.4, 29.5, 29.0, 28.8, 13.9 HRMS (EI) Calcd for C43H42N4S4: 742.22923 [M+•] Found m/z=742.22805. UV-Vis (CHCl$_3$): λ$_{max}$ 425 nm (ε=28000 M$^{-1}$ cm$^{-1}$).

5',5"-bis(4-2,1,3-benzothiadiazole)-2,7-bis(3-hexyl-2-thienyl)-1,6-methano[10]annulene (Tail In BTMTB) (Prepared According to General Stille Small Molecule Procedure)

5',5"-bis(tributylstannyl)-2,7-bis(3-hexyl-2-thienyl)-1,6-methano[10]annulene (100.0 mg, 0.0950 mmol), 4-bromo-2,1,3-benzothiadiazole (42.9 mg, 0.1995 mmol), (PPh3)4PdCl2 (3.3 mg, 0.0047 mmol), and toluene (5 mL). Yielded 10.9 mg of a red powder (15%). 1H NMR (400 MHz, CDCl$_3$) δ: 8.11 (d, J=7.5 Hz, 2H), 8.02 (m, 1H), 7.88 (m, 2H), 7.61 (m, 2H), 7.53 (dd, J=2.5, 9.0 Hz, 2H), 7.36 (dd, J=3.1, 9.4 Hz, 2H), 7.14 (t, J=9.4 Hz, 2H), 3.06 (m, 2H), 2.89 (m, 2H), 1.70 (m, 4H), 1.22 (m, 12H), 0.82 (m, 6H), 0.03 (s, 2H). HRMS (EI) Calcd for C43H42N4S4 [M+•]: 742.22923 Found m/z=742.23034. UV-Vis (CHCl$_3$): λ$_{max}$ 446 nm (ε=19000 M$^{-1}$ cm$^{-1}$).

5',5"-bis(4-2,1,3-benzothiadiazole)-2,7-bis(2-thienyl)-1,6-methano[10]annulene (No Tail BTMTB) (Prepared According to General Stille Small Molecule Procedure)

5',5"-bis(tributylstannyl)-2,7-bis(2-thienyl)-1,6-methano[10]annulene (150.0 mg, 0.1692 mmol), 4-bromo-2,1,3-benzothiadiazole (7.5 mg, 0.36 mmol), (PPh$_3$)$_4$PdCl$_2$ (5.9 mg, 0.0090 mmol), and toluene (3 mL). Yielded 4.6 mg of a red powder (5%). 1H NMR (400 MHz, CDCl$_3$) δ: 8.21 (d, J=3.9 Hz, 2H), 7.98 (d, J=8.8 Hz), 7.95 (s, 2H), 7.89 (d, J=8.8 Hz, 2H), 7.63 (d, J=3.9 Hz, 2H), 7.55 (d, J=9.9 Hz, 2H), 7.51 (dd, J=3.5 Hz, 1 Hz, 2H), 7.46 (d, J=9.8 Hz, 2H), 7.39 (dd, J=5.0 Hz, 1 Hz, 2H), 7.19-7.13 (m, 6H), 0.07 (s, 2H). UV-Vis (CHCl$_3$): λ$_{max}$ 509 nm (ε=19000 M$^{-1}$ cm$^{-1}$).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Zhokhavets, U.; Erb, T.; Hoppe, H.; Gobsch, G.; Sariciftci, N. S. Thin Solid Films 2006, 496, 679.

Sivula, K.; Luscombe, C. K.; Thompson, B. C.; Fréchét, J. M. J. J. Am. Chem. Soc. 2006, 128, 13988.

Brabec, C. J. Sol. Energy Mater. Sol. Cells 2004, 83, 273.

Yip, H.-L.; Jen, A. K.-Y. Energy Environ. Sci. 2012, 5, 5994.

Chen, T.-A.; Rieke, R. D. Synth. Met. 1993, 60, 175.

Chen, T.-A.; Wu, X.; Rieke, R. D. J. Am. Chem. Soc. 1995, 117, 233.

McCullough, R. D.; Tristram-Nagle, S.; Williams, S. P.; Lowe, R. D.; Jayaraman, M. J. Am. Chem. Soc. 1993, 115, 4910.

McCullough, R. D.; Lowe, R. D. J. Chem. Soc., Chem. Commun 1992, 70.

McCullough, R. D.; Williams, S. P.; Tristram-Nagle, S.; Jayaraman, M.; Eqbank, P. C.; Miller, L. Synth. Met. 1995, 69, 279.

McCullough, R. D.; Lowe, R. D.; Jayaraman, M.; Anderson, D. L. J. Org. Chem. 1993, 58, 904-912.

Woo, C. H.; Thompson, B. C.; Bumjoon, J. K.; Toney, M. F.; Frechet, J. M. J. J. Am. Chem. Soc. 2008, 130, 16324.

Jayakannan, M.; Van Hal, P. A.; Janssen, R. A. J. J. Polym Sci., Part A: Polym. Chem. 2002, 40, 251.

Mondal, R.; Ko, S.; Verploegen, E.; Becerril, H. A.; Toney, M. F.; Bao, Z. J. Mater. Chem. 2011, 21, 1537.

Ding, J.; Li, Z.; Cui, Z.; Robertson, G. P.; Song, N.; Du, X.; Scoles, L. J. Polym Sci., Part A: Polym. Chem. 2011, 49, 3374.

Lee, S. K.; Cho, S.; Tong, M.; Seo, J. H.; Heeger, A. J. J. Polym. Sci., Part A: Polym. Chem. 2011, 49, 1821.

Elsenbaumer, R. L.; Jen, K.-Y.; Miller, G. G.; Eckhardt, H.; Shacklette, L. W.; Jow, R. In Electronic Properties of Conjugated Polymers; Kuzmany, H., Mehring, M., Roth, S., Eds.; Springer Series in Solid State Sciences; Springer: Berlin, 1987; Vol. 76, p 400.

Souto-Maior, R. M.; Hinkelmann, K.; Wudl, F. Macromolecules 1990, 23, 1268.

Zagorska, M.; Kulszewicz-Bajer, I.; Pron, A.; Firlcj, L.; Berier, P.; Galtier, G. Synth. Met. 1991, 45, 385.

Zagorska, M.; Krishe, B. Polymer 1990, 31, 1379.

Krishe, B.; Hellberg, J.; Lilja, C. J. Chem. Soc., Chem. Commun. 1987, 19, 1476.

McCullough, R. D. Adv. Mater. 1998, 10, 93.

Hong, S. Y.; Kim, C. Y.; Kim, D. Y.; Hoffman, R. Macromolecules 2001, 34, 6475.

Havinga, E. E.; ten Hoeve, W.; Wynberg, H. Polym. Bull. 1992, 29, 119.

Havinga, E. E.; ten Hoeve, W.; Wynberg, H. Synth. Met. 1993, 55-57, 299.

Peart, P. A.; Tovar, J. D. Org. Left. 2007, 9, 3041.

Peart, P. A.; Repka, L. M.; Tovar, J. D. Eur. J. Org. Chem. 2008, 2193.

Peart, P. A.; Tovar, J. D. Macromolecules 2009, 42, 4449.

Peart, P. A.; Elbaz, G.; Tovar, J. D. Pure Appl. Chem. 2010, 82, 1045.

Vogel, E.; Roth, H. D. Angew. Chem. 1964, 76, 145.

Hummelen, J. C.; Knight, B. W.; LePeq, F.; Wudl, F.; Wilkins, C. J. Org. Chem. 1995, 60, 532-538.

Sirringhaus, H. Adv. Mater. 2005, 17, 2411.

Baek, N. S.; Hau, S. K.; Yip, H.-L.; Acton, O.; Chen, K.-S.; Jen, A. K.-Y. Chem. Mater. 2008, 20, 5734.

Osaka, I.; Zhang, R.; Sauvé, G.; Smilgies, D.-M.; Kowalewski, T.; McCullough, R. D. J. Am. Chem. Soc. 2009, 131, 2521.

Bryant-Friedrich, A. C.; Neidlein, R. Helv. Chim. Acta 1997, 80, 128.

Bryant-Friedrich, A. C.; Neidlein, R. Helv. Chim. Acta 1997, 80, 1639.

Mee, S. P. H.; Lee, V.; Baldwin, J. E. Angew. Chem., Int. Ed. 2004, 43, 1132.

Karikomi, M.; Kitamura, C.; Tanaka, S.; Yamashita, Y. J. Am. Chem. Soc. 1995, 117, 6791-6792.

Bijleveld, J. C.; Zoombelt, A. P.; Mathijssen, S. G. J.; Wienk, M. M.; Turbiex, M.; de Leeuw, D. M.; Janssen, R. A. J. J. Am. Chem. Soc. 2009, 131, 16616.

Woo, C. H.; Beaujuge, P. M.; Holcombe, T. W.; Lee, O. P.; Fréchet, J. M. J. J. Am. Chem. Soc. 2010, 132, 15547.

Holdcroft, S. J. Polym. Sci., Part B: Polym. Phys. 1991, 29, 1585-1588.

(34) Wohlgenannt, M.; Jiamng, X. M.; Vardeny, Z. V. Phys. Rev. B 2004, 69, 241204(R).

Brédas, J. L. J. Chem. Phys. 1985, 82, 3809.

McCullough, R. D. Adv. Mater. 1998, 10, 93.

Zou, Y.; Gendron, D.; Neagu-Plesu, R.; Leclerc, M. Macromolecules 2009, 42, 6361.

Pommerehne, J.; Vestweber, H.; Guss, W.; Mahrt, R. F.; Baessler, H.; Porsch, M.; Daub, J. Adv. Mater. 1995, 7, 551.

Brabec, C. J., Dyakonov, V., Scherf, U., Eds.; Organic Photovoltaics; Wiley-VCH: New York, 2008.

McCullough, R. D.; Tristram-Nagle, S.; Williams, S. P.; Lowe, R. D.; Jayaraman, M. J. Am. Chem. Soc. 1993, 115, 4910.

Sonar, P.; Singh, S. P.; Li, Y.; Soh, M. S.; Dodabalapur, A. Adv. Mater. 2010, 22, 5409.

Li, Y.; Sonar, P.; Singh, S. P.; Zeng, W.; Soh, M. S. J. Mater. Chem. 2011, 21, 10829.

Chua, L.-L.; Zaumseil, J.; Chang, J.-F.; Ou, E. C.-W.; Ho, P. K.-H.; Sirringhaus, H.; Friend, R. H. Nature 2005, 434, 194.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A compound of Formula (I) or Formula (II):

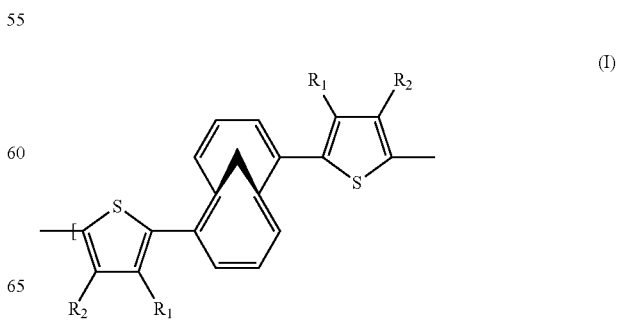

-continued

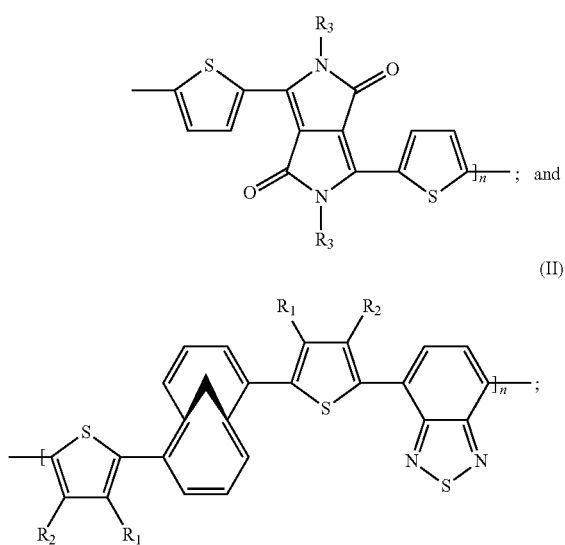

(II)

wherein:
n is an integer selected from the group consisting of 1 to 150; and
$R_1$, $R_2$, and, $R_3$ are each independently selected from the group consisting of H and $C_6$-$C_{20}$ linear or branched alkyl.

2. The compound of claim 1, wherein $R_3$ is $C_8H_{17}$ and the compound of Formula (I) is selected from the group consisting of:

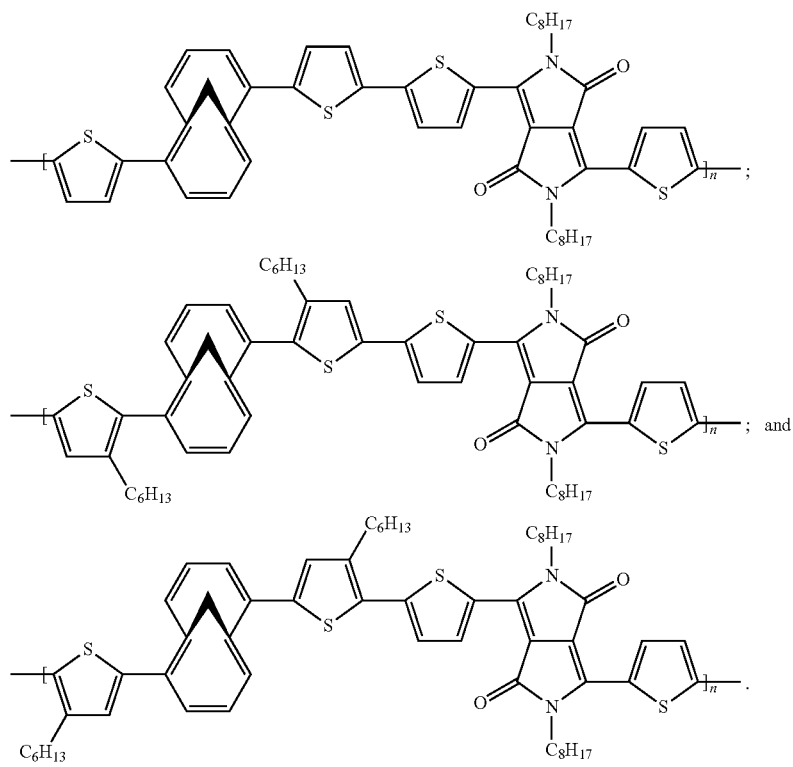

3. The compound of claim 1, wherein the compound of Formula (II) is selected from the group consisting of:

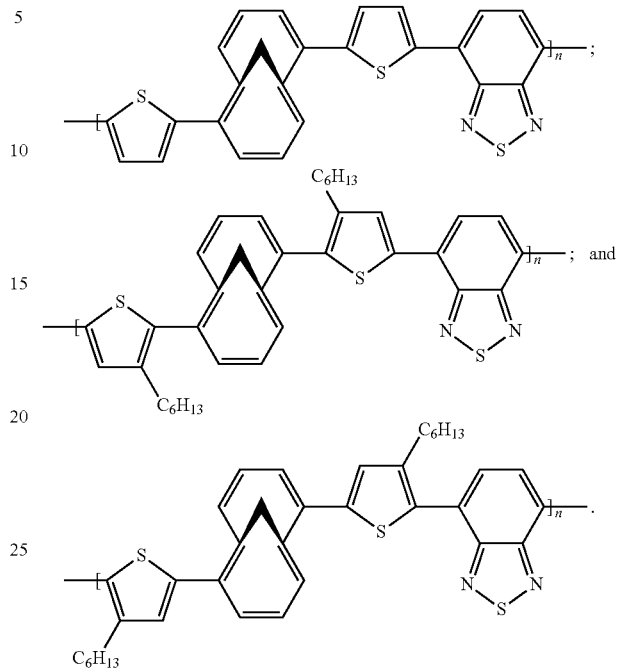

4. The compound of claim 1, wherein n is selected from the group consisting of 2, 3, 4, and 5.

5. A monomer of a compound of Formula (II), wherein the monomer is a compound of Formula (III):

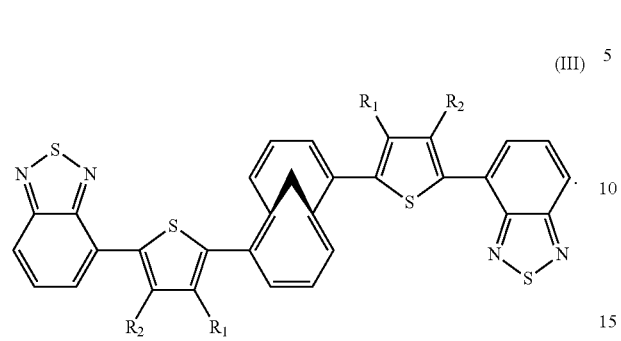

(III)

6. The monomer of claim 5, wherein the compound of Formula (III) is selected from the group consisting of:

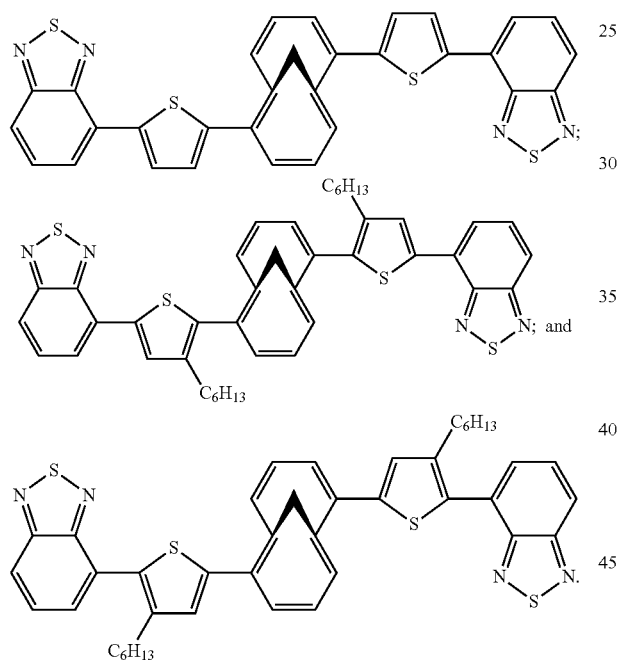

7. A film comprising a compound of Formula (I) or Formula (II):

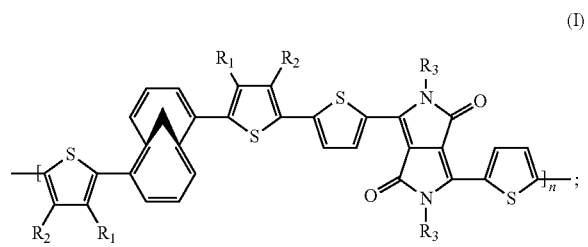

(I)

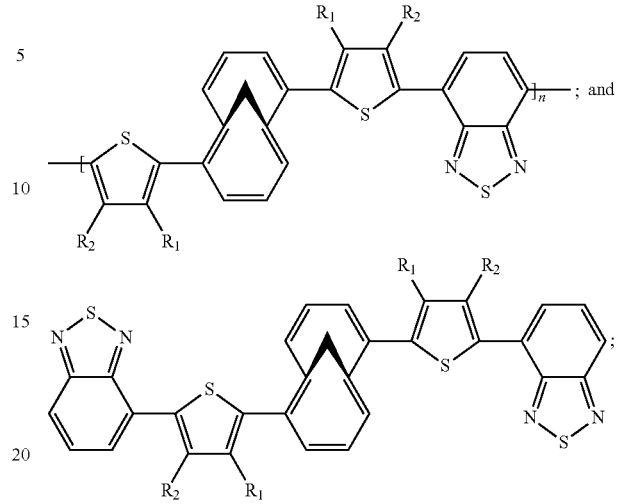

(II)

wherein:
  n is an integer selected from the group consisting of 1 to 150; and
  $R_1$, $R_2$, and, $R_3$ are each independently selected from the group consisting of H and $C_6$-$C_{20}$ linear or branched alkyl.

8. The film of claim 7, further comprising a blend of a compound of Formula (I) or Formula (II) and one or more of an electron donating material and an electron accepting material.

9. The film of claim 8, wherein the electron accepting material comprises a fullerene.

10. The film of claim 9, wherein the fullerene comprises [6,6]-phenyl-$C_{61}$-butyric acid methyl ester (PCBM).

11. The film of claim 8, wherein the electron donating material is selected from the group consisting of poly(3-hexyl thiophene) (P3HT) and 2-methoxy-5-(2'-ethylhexyloxy)-p-phenylene vinylene (MEH-PPV).

12. A device comprising the film of claim 7.

13. The device of claim 12, wherein the device comprises a bulk heterojunction organic photovoltaic (BHJ-OPV) device.

14. The device of claim 12, wherein the device comprises a layered device in which at least one of a p-channel layer and an n-channel layer comprises a compound of Formula (I) or Formula (II).

15. A device comprising a compound of Formula (I) or Formula (II):

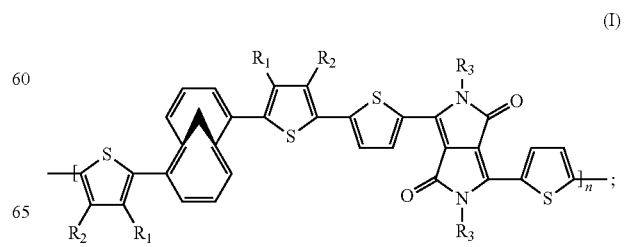

(I)

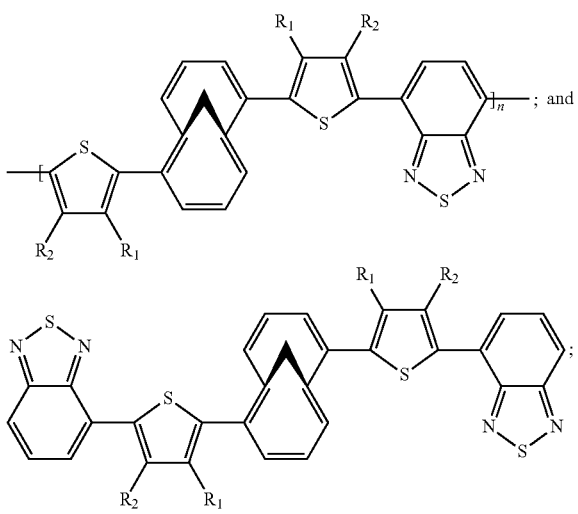

wherein:
n is an integer selected from the group consisting of 1 to 150; and
$R_1$, $R_2$, and, $R_3$ are each independently selected from the group consisting of H and $C_6$-$C_{20}$ linear or branched alkyl.

16. The device of claim 15, wherein the device comprises an organic semiconductor.

17. The device of claim 15, wherein the device is selected from the group consisting of a thermoelectric device and an organic photovoltaic device.

18. The device of claim 15, wherein the device comprises a field-effect transistor.

19. The device of claim 15, wherein the field-effect transistor comprises a p-type field-effect transistor.

20. The device of claim 18, wherein the field-effect transistor comprises a device selected from the group consisting of a display element, an electronic tag, an electromagnetic sensor, and a pressure sensor.

* * * * *